United States Patent [19]

Katsuda et al.

[11] Patent Number: 4,457,940
[45] Date of Patent: Jul. 3, 1984

[54] CARBOXYLIC ACID ESTER DERIVATIVES, PROCESS FOR MANUFACTURING SAID DERIVATIVES, INSECTICIDES AND ACARICIDES CONTAINING SAID DERIVATIVES, AND METHOD FOR KILLING INSECTS AND ACARINA BY TREATING THEREWITH

[75] Inventors: Yoshio Katsuda, Nishinomiya; Hajime Hirobe; Yoshihiro Minamite, both of Toyonaka, all of Japan

[73] Assignee: Dainippon Jochugiku Kabushiki Kaisha, Osaka, Japan

[21] Appl. No.: 333,451

[22] Filed: Dec. 22, 1981

[30] Foreign Application Priority Data

Dec. 27, 1980 [JP] Japan .................................. 55-185758
Jan. 31, 1981 [JP] Japan .................................. 56-13147
Apr. 7, 1981 [JP] Japan .................................. 56-52729
Apr. 21, 1981 [JP] Japan .................................. 56-60070

[51] Int. Cl.³ .................... C09B 23/10; A01N 43/36; A01N 37/08; A01N 37/10
[52] U.S. Cl. .................................. 424/274; 549/323; 549/66; 560/124; 424/306; 424/308; 424/305; 424/275; 424/285; 424/304; 548/543; 260/465 D
[58] Field of Search .................. 542/429; 549/323, 66, 549/444, 447; 260/326.45, 465 D; 560/124; 424/306, 308, 305, 274, 275, 285, 304; 548/543

[56] References Cited

U.S. PATENT DOCUMENTS 4,113,968 9/1978 Mori et al. .......................... 549/66

OTHER PUBLICATIONS

Noller, Textbook of Organic Chemistry, 2nd Ed., W. B. Saunders Co., Philadelphia, Pa., 1958, p. 128.

Primary Examiner—Henry R. Jiles
Assistant Examiner—Robert C. Whittenbaugh
Attorney, Agent, or Firm—Parkhurst & Oliff

[57] ABSTRACT

Novel carboxylic acid ester derivatives, of the formula (I):

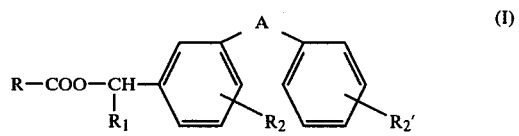

process for manufacturing said derivatives, insecticides and acaricides containing said derivatives, and a method for killing insects and acarina by treating therewith.

20 Claims, No Drawings

CARBOXYLIC ACID ESTER DERIVATIVES, PROCESS FOR MANUFACTURING SAID DERIVATIVES, INSECTICIDES AND ACARICIDES CONTAINING SAID DERIVATIVES, AND METHOD FOR KILLING INSECTS AND ACARINA BY TREATING THEREWITH

DETAILED DESCRIPTION OF THE INVENTION

The present invention relates to a compound of the formula (I):

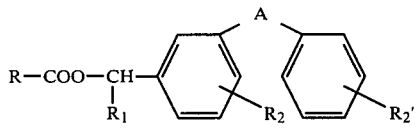 (I)

wherein R denotes the group (II), (III), (IV), (V), (VI), (VII), (VIII), (IX), (X), (XI), (XII) or (XIII):

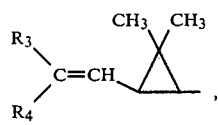 (II)

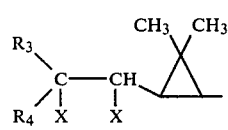 (III)

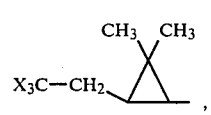 (IV)

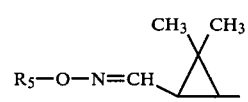 (V)

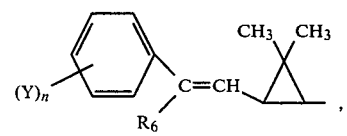 (VI)

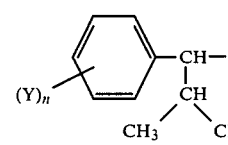 (VII)

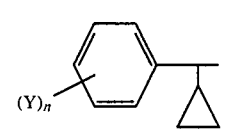 (VIII)

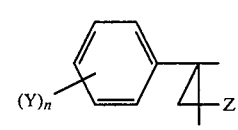 (IX)

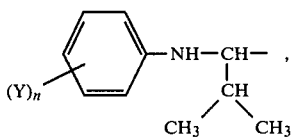 (X)

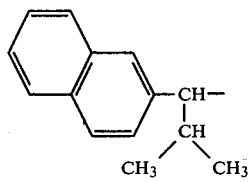 (XI)

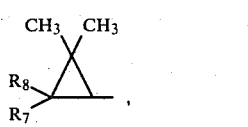 (XII)

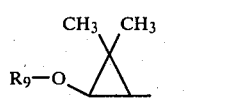 (XIII)

wherein $R_3$ and $R_4$, which are the same as or different from each other, denote methyl group, halogen atom, or halomethyl group, or $R_3$ and $R_4$ together may form the ring:

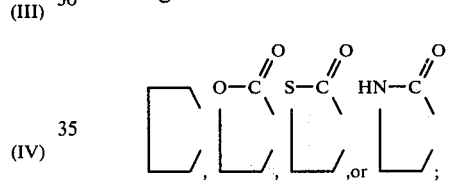

X denotes halogen atom; $R_5$ denotes alkyl group having 1-3 carbon atoms; n is an integer of 1-3, $R_6$ denotes hydrogen atom, methyl group, halogen atom, or cyano group; Y denotes hydrogen atom, halogen atom, lower alkyl group, lower alkoxy group, lower alkylthio group, lower haloalkyl group, lower haloalkoxy group, lower haloalkylthio group, or methylenedioxy group; z denotes methyl group, fluorine atom, or chlorine atom; $R_7$ denotes methyl group, or chlorine atom; $R_8$ denotes methyl group, chlorine atom, halomethyl group, methoxy group, or methoxymethyl group, or $R_7$ and $R_8$ together may form ethylene-, trimethylene-, or tetramethylene-chain; $R_9$ denotes alkyl-group having 1-6 carbon atoms, or cycloalkyl-, alkenyl-, haloalkyl-, aloalkenyl- or alkynyl-group or the group of the formula (XIV):

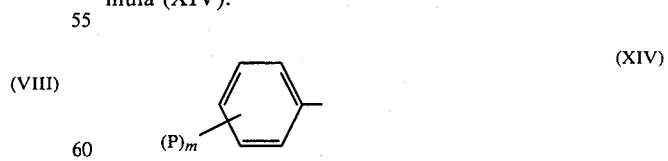 (XIV)

wherein m is an integer of 1-2; P denotes hydrogen atom, halogen atom, lower alkyl group, lower alkoxy group, lower alkylthio group, lower haloalkyl group, lower haloalkoxy group, or methylenedioxy group; $R_1$ denotes hydrogen atom, cyano group, methyl group, or ethynyl group; $R_2$, $R_2'$ denote hydrogen atom, halogen atom, methyl group, trifluoromethyl group or lower alkoxy group; A denotes the group of the formula (XV) or (XVI):

 (XV)

 (XVI)

wherein $R_{10}$ denotes hydrogen atom, alkyl-, or haloalkyl-group having 1–2 carbon atoms, halogen atom, formyl group, acetyl group or haloacetyl group, provided that the group of the formula (XV) may denote that the nitrogen atom may form a salt of a strong inorganic acid or a strong organic acid; $R_{11}$ denotes hydrogen atom or fluorine atom; and $R_{12}$ denotes halogen atom, lower alkyl group, lower haloalkyl group or lower alkoxy group.

The present invention also relates to an insecticide and an acarinas containing the compound of the formula (I) as an active ingredient and a process for manufacturing the compound of the formula (I).

Recently, there have been widely made the developments and researches as to the analogous substances having the modified chemical structures of the pyrethrine occurring in nature as insecticidal ingredients. A number of the compounds of the formula (IXX):

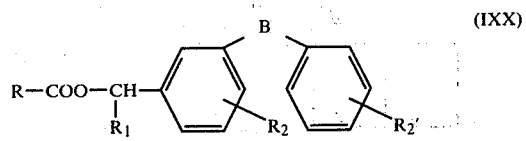 (IXX)

wherein B is oxygen atom or methylene group and R, $R_1$, $R_2$ and $R_2'$ have the same meanings as mentioned above, have been known and some of them have been put into practical use for households, the prevention of diseases and agricultural insecticides. However, the toxicity toward fish of these compounds is extremely high and therefore, there has been room for improvement in their properties.

After strenuous studies of new compounds useful as an insecticidal ingredient, the present inventors have accomplished the present invention based on the knowledge that the compounds of the general formula (I) in which "B" in the general formula (IXX) is replaced by unsubstituted or substituted amino group of the formula (XV) or the substituted methylene group of the formula (XVI) exhibit extremely high insecticidal effects against a variety of hygienic and agricultural insects, but exhibit more reduced toxicity against warm blooded animals and fish compared with their corresponding original compounds in which B is not substituted. According to the conventional knowledge, the compounds of the formula (IXX) in which B is methylene group are inferior by several times in terms of insecticidal activities compared with those in which B is oxygen. Therefore, it is unexpected and surprising that the compounds according to the present invention in which "B" in the formula (IXX) is substituted with the above-mentioned groups exhibit far increased insecticidal activities.

The compounds of the formula (I) according to the present invention can be produced in accordance with the ordinary esterification method. That is, they can be produced by reacting a carboxylic acid of the general formula (XVII):

R—COOH (XVII)

wherein R denotes the group (II), (III), (IV), (V), (VI), (VII), (VIII), (IX), (X), (XI), (XII) or (XIII):

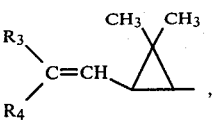 (II)

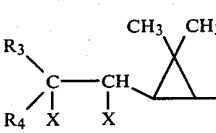 (III)

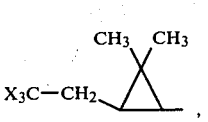 (IV)

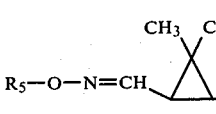 (V)

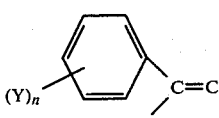 (VI)

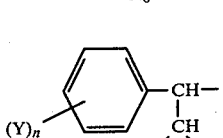 (VII)

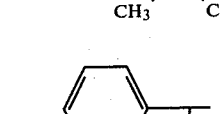 (VIII)

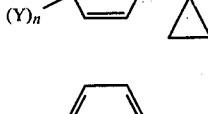 (IX)

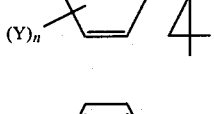 (X)

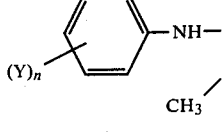 (XI)

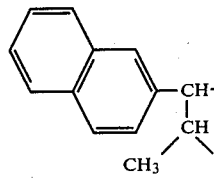

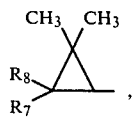
(XII)

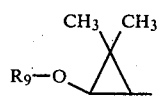
(XIII)

wherein R$_3$ and R$_4$, which are the same as or different from each other, denote methyl group, halogen atom, or halomethyl group, or R$_3$ and R$_4$ together may form the ring:

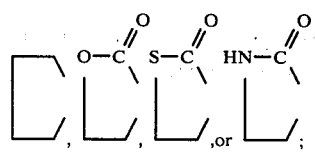

X denotes halogen atom; R$_5$ denotes C$_1$–C$_3$ alkyl group; n is an integer of 1–3, R$_6$ denotes hydrogen atom, methyl group, halogen atom, or cyano group; Y denotes hydrogen atom, halogen atom, lower alkyl group, lower alkoxy group, lower alkylthio group, lower haloalkyl group, lower haloalkoxy group, lower haloalkylthio group, or methylenedioxy group; z denotes methyl group, fluorine atom, or chlorine atom; R$_7$ denotes methyl group, or chlorine atom; R$_8$ denotes methyl group, chlorine atom, halomethyl group, methoxy group, or methoxymethyl group, or R$_7$ and R$_8$ together may form ethylene-, trimethylene-, or tetramethylene-chain; R$_9$ denotes alkyl-group having 1–6 carbon atoms or cycloalkyl-, alkenyl-, haloalkyl-, aloalkenyl-, or alkynyl-group, or the group of the formula (XIV):

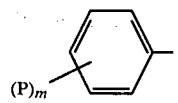
(XIV)

wherein m is an integer of 1–2; P denotes hydrogen atom, halogen atom, lower alkyl group, lower alkoxy group, lower alkylthio group, lower haloalkyl group, lower haloalkoxy group, or methylenedioxy group; or a reactive derivative thereof, with an alcohol of the general formula (XVIII):

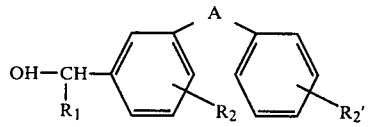
(XVIII)

wherein R$_1$ denotes hydrogen atom, cyano group, methyl group, or ethynyl group; R$_2$, R$_2'$ denote hydrogen atom, halogen atom, methyl group, trifluoromethyl group or lower alkoxy group; A denotes the group of the formula (XV) or (XVI):

(XV)

(XVI)

wherein R$_{10}$ denotes hydrogen atom, alkyl-, or haloalkyl-group having 1–2 carbon atoms, halogen atom, formyl group, acetyl group or haloacetyl group, provided that the group of the formula (XV) may denote that the nitrogen atom may form a salt of a strong inorganic acid or a strong organic acid; R$_{11}$ denotes hydrogen atom or fluorine atom; and R$_{12}$ denotes halogen atom, lower alkyl group, lower haloalkyl group or lower alkoxy group, or a reactive derivative thereof.

As a reactive derivative of the carboxylic acid, for instance, acid halide, acid anhydride, lower alkyl ester, alkali metal salt, or the like can be employed. As an alcohol reactive derivative, for instance, chloride, bromide, p-toluene sulfonate or the like can be employed. The reaction is carried out in an appropriate solvent, and if necessary in the presence of deoxidation agent, or organic or inorganic acid or base as catalyzer, and if necessary under heating. Except the compounds in which both R$_7$ and R$_8$ in an acid component in the general formula (I) are methyl group, at least one asymmetric carbon atom is present and therefore, the compounds according to the present invention, made in accordance with the ordinary method, fall within the scope of the present invention.

As a result of the present inventors earnestly studying the optical and geometrical isomers of halovinyl chrysanthemumic acids, it has been found that the isomers having the configuration (1R, 3S), i.e., α-cis form in the general formula (II) have far superior insecticidal effects compared with the other isomers. There have been consecutively developed the methods of selectively synthesizing the dihalovinyl chrysanthemumic acid of cis form and improved methods for separating the dl forms (See Pestic. Sci. 1980, 11 180), and therefore, it is understood that it is so useful to discover the isomers excellent in insecticidal activities.

As regards the alcohol components, the asymmetric carbon is present except the compounds in which R$_1$ is hydrogen atom. The compounds produced in accordance with the ordinary method comprise a RS racemic form and these isomers fall within the scope of the present invention. As in the case with the phenoxybenzyl alcohol ester derivatives, the alcohol components of S form are preferable in terms of insecticidal activities.

The typical compounds according to the present invention are shown below, but they are merely illustrative of the present invention and are not intended for limiting the scope of the present invention.

(1)
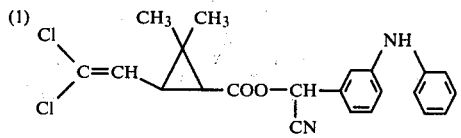

3'-anilino-α'-cyanobenzyl 2,2-dimethyl-3-(2,2-dichlorovinyl) cyclopropane carboxylate, $n^{20}_D$ 1.5691

(2) 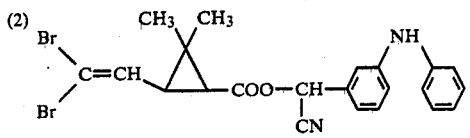

3'-anilino-α'-cyanobenzyl 2,2-dimethyl-3-(2,2-dibromovinyl)cyclopropane carboxylate, $n^{20}_D$ 1.5774

(3) 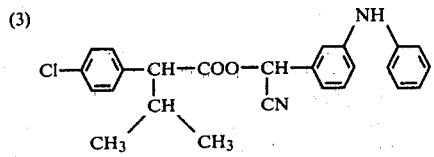

3'-anilino-α'-cyanobenzyl 2-(4-chlorophenyl)isovalerate, $n^{20}_D$ 1.5740

(4) 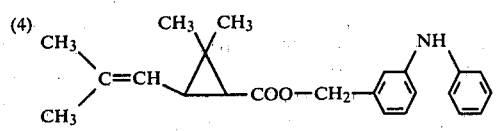

3'-anilinobenzyl 2,2-dimethyl-3-(2,2-dimethylvinyl) cyclopropane carboxylate, $n^{20}_D$ 1.5686

(5) 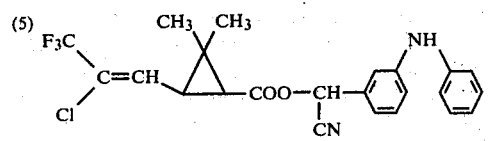

3'-anilino-α'-cyanobenzyl 2,2-dimethyl-3-(2-chloro-2-trifluoromethylvinyl)cyclopropane carboxylate, $n^{20}_D$ 1.5679

(6) 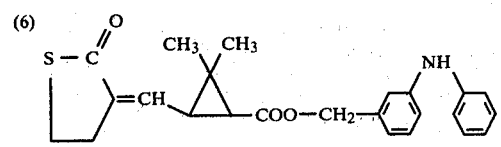

3'-anilinobenzyl 2,2-dimethyl-3-(2-oxothien-3-ylidenmethyl)cyclopropane carboxylate, $n^{20}_D$ 1.5761

(7) 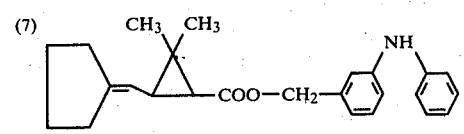

3'-anilinobenzyl 2,2-dimethyl-3-cyclopentylidenemethylcyclopropane carboxylate, $n^{20}_D$ 1.5634

(8) 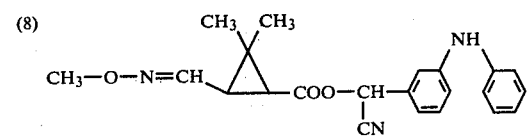

3'-anilino-α'-cyanobenzyl 2,2-dimethyl-3-methoxyiminomethylcyclopropane carboxylate, $n^{20}_D$ 1.5640

(9) 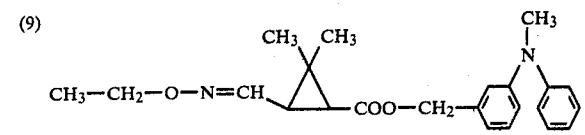

3'-(N-methylanilino)-benzyl 2,2-dimethyl-3-ethoxyiminomethylcyclopropane carboxylate, $n^{20}_D$ 1.5662

(10) 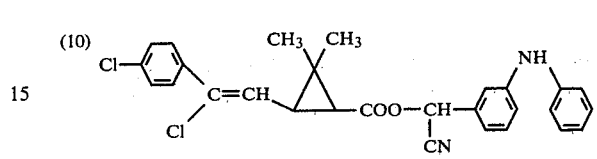

3'-anilino-α'-cyanobenzyl 2,2-dimethyl-3-[2-chloro-2-(4-chlorophenyl)vinyl]cyclopropane carboxylate, $n^{20}_D$ 1.5991

(11) 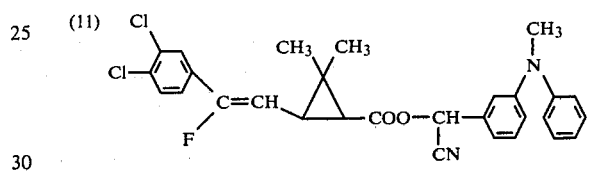

3'-(N-methylanilino)-α'-cyanobenzyl 2,2-dimethyl-3-[2-fluoro-2-(3,4-dichlorophenyl)vinyl]cyclopropane carboxylate, $n^{20}_D$ 1.5958

(12) 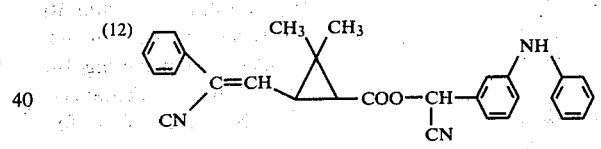

3'-anilino-α'-cyanobenzyl 2,2-dimethyl-3-(2-cyano-2-phenylvinyl)cyclopropane carboxylate, $n^{20}_D$ 1.5974

(13) 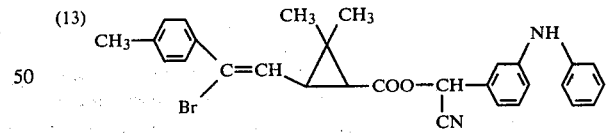

3'-anilino-α'-cyanobenzyl 2,2-dimethyl-3-[2-bromo-2-(4-methylphenyl)vinyl]-cyclopropane carboxylate, $n^{20}_D$ 1.6013

(14) 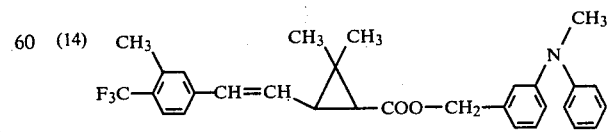

3'-(N-methylanilino)benzyl 2,2-dimethyl-3-[2-(3-methyl-4-trifluoromethylphenyl)vinyl]cyclopropane carboxylate, $n^{20}_D$ 1.5904

(15) 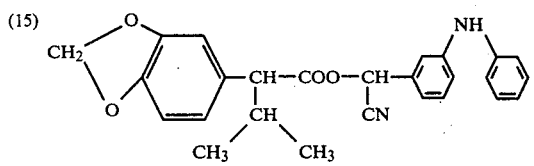

3'-anilino-α'-cyanobenzyl α-(3,4-methylenedioxyphenyl) isovalerate, $n^{20}_D$ 1.5771

(16) 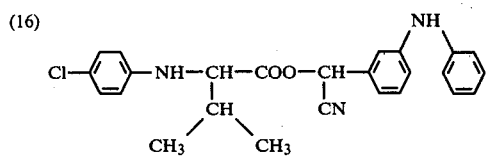

3'-anilino-α'-cyanobenzyl α-(4-chloroanilino)-isovalerate, $n^{20}_D$ 1.5837

(17) 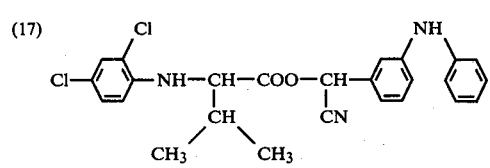

3'-anilino-α'-cyanobenzyl α-(2,4-dichloroanilino)isovalerate, $n^{20}_D$ 1.5946

(18) 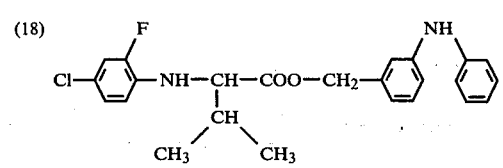

3'-anilinobenzyl α-(2-fluoro-4-chloroanilino)isovalerate, $n^{20}_D$ 1.5882

(19) 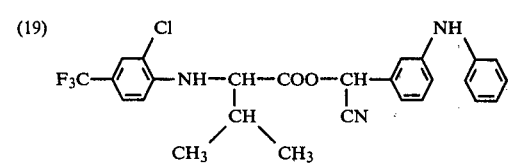

3'-anilino-α'-cyanobenzyl α-(2-chloro-4-trifluoromethylanilino)-isovalerate, $n^{20}_D$ 1.5987

(20) 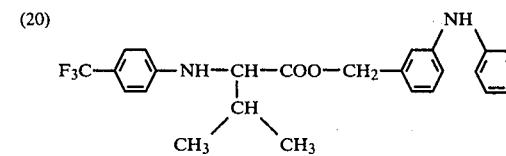

3'-anilinobenzyl α-(4-trifluoromethylanilino)-isovalerate, $n^{20}_D$ 1.5840

(21) 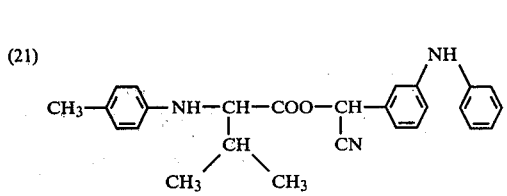

3'-anilino-α'-cyanobenzyl α-(4-methylanilino)isovalerate, $n^{20}_D$ 1.5855

(22) 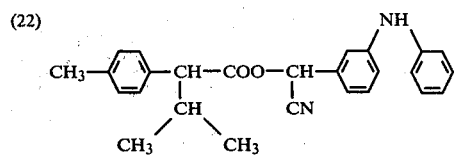

3'-anilino-α'-cyanobenzyl α-(4-methylphenyl) isovalerate, $n^{20}_D$ 1.5734

(23) 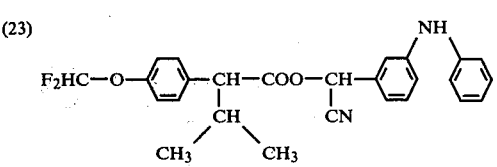

3'-anilino-α'-cyanobenzyl α-(4-difluoromethoxyphenyl)isovalerate, $n^{20}_D$ 1.5733

(24) 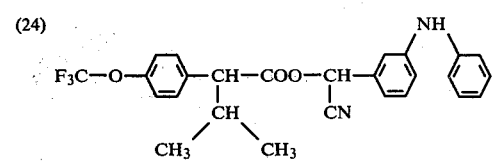

3'-anilino-α'-cyanobenzyl α-(4-trifluoromethoxyphenyl)isovalerate, $n^{20}_D$ 1.5828

(25) 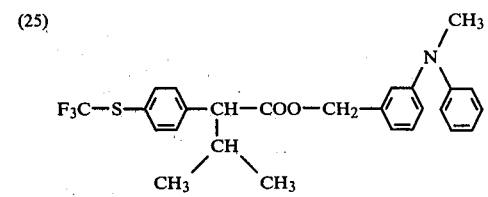

3'-(N-methylanilino)benzyl α-(4-trifluoromethylthiophenyl)isovalerate, $n^{20}_D$ 1.5971

(26) 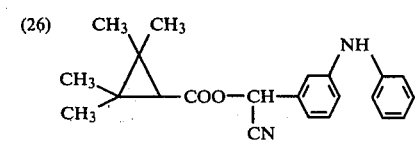

3'-anilino-α'-cyanobenzyl 2,2,3,3-tetramethylcyclopropane carboxylate, $n^{20}_D$ 1.5596

(27) 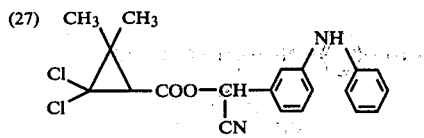

3'-anilino-α'-cyanobenzyl 2,2-dimethyl-3,3-dichlorocyclopropane carboxylate, $n^{20}_D$ 1.5633

(28) 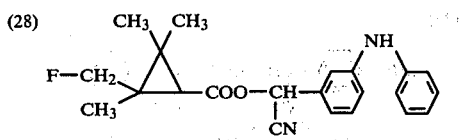

3'-anilino-α'-cyanobenzyl 2,2,3-trimethyl-3-fluoromethylcyclopropane carboxylate, $n^{20}_D$ 1.5584

(29) 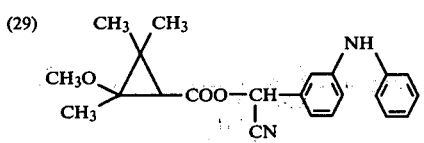

3'-anilino-α'-cyanobenzyl 2,2,3-trimethyl-3-methoxycyclopropane carboxylate, $n^{20}_D$ 1.5619

(30) 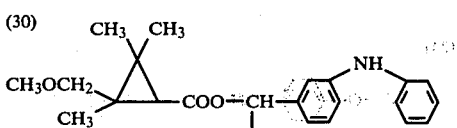

3'-anilino-α'-cyanobenzyl 2,2,3-trimethyl-3-methoxymethylcyclopropane carboxylate, $n^{20}_D$ 1.5680

(31) 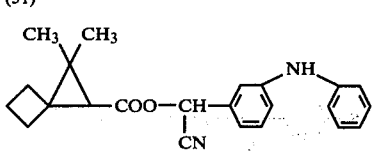

3'-anilino-α'-cyanobenzyl 2,2-dimethyl-3,3-trimethylenecyclopropane carboxylate, $n^{20}_D$ 1.5625

(32) 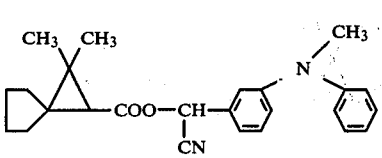

3'-(N-methylanilino)-α'-cyanobenzyl 2,2-dimethyl-3,3-tetramethylenecyclopropane carboxylate, $n^{20}_D$ 1.5718

(33) 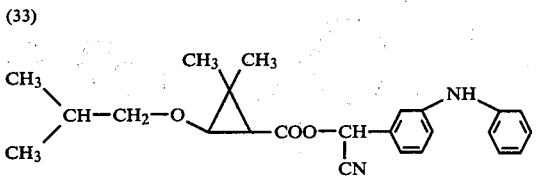

3'-anilino-α'-cyanobenzyl 2,2-dimethyl-3-isobutoxycyclopropane carboxylate, $n^{20}_D$ 1.5850

(34) 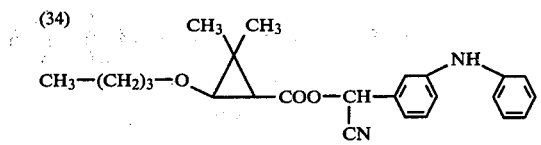

3'-anilino-α'-cyanobenzyl 2,2-dimethyl-3-n-butoxycyclopropane carboxylate, $n^{20}_D$ 1.5852

(35) 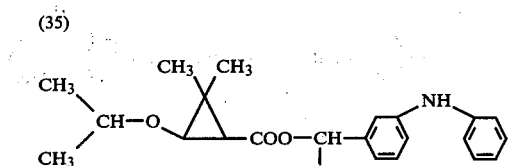

3'-anilino-α'-cyanobenzyl 2,2-dimethyl-3-isopropoxycyclopropane carboxylate, $n^{20}_D$ 1.5794

(36) 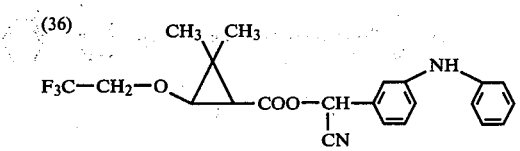

3'-anilino-α'-cyanobenzyl 2,2-dimethyl-3-(2,2,2-trifluoroethoxy)cyclopropane carboxylate, $n^{20}_D$ 1.5809

(37) 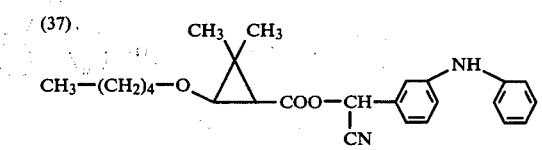

3'-anilino-α'-cyanobenzyl 2,2-dimethyl-3-n-amyloxycyclopropane carboxylate, $n^{20}_D$ 1.5896

(38) 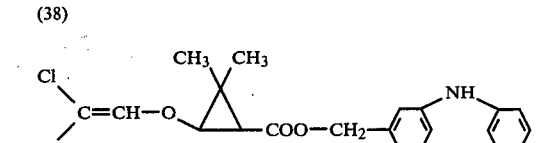

3'-anilinobenzyl 2,2-dimethyl-3-(2,2-dichlorovinyloxy)-cyclopropane carboxylate, $n^{20}_D$ 1.5845

(39) 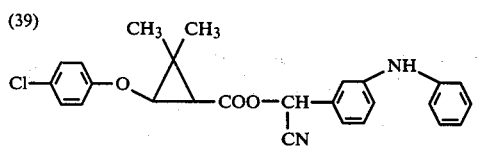

3'-anilino-α'-cyanobenzyl 2,2-dimethyl-3-(4-chlorophenoxy)cyclopropane carboxylate, $n^{20}_D$ 1.5961

(40) 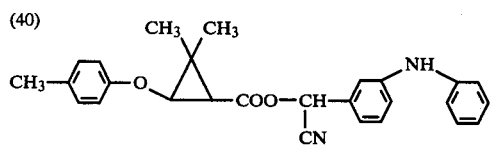

3'-anilino-α'-cyanobenzyl 2,2-dimethyl-3-(4-methylphenoxy)cyclopropane carboxylate, $n^{20}_D$ 1.5948

(41) 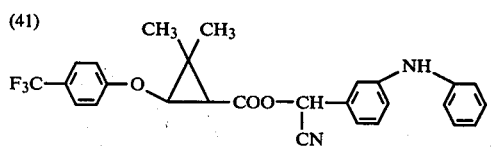

3'-anilino-α'-cyanobenzyl 2,2-dimethyl-3-(4-trifluoromethylphenoxy)cyclopropane carboxylate, $n^{20}_D$ 1.5937

(42) 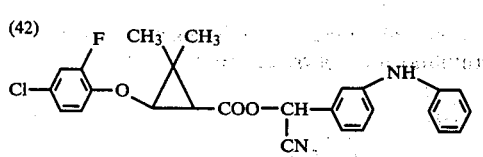

3'-anilino-α'-cyanobenzyl 2,2-dimethyl-3-(2-fluoro-4-chlorophenoxy)cyclopropane carboxylate, $n^{20}_D$ 1.5976

(43) 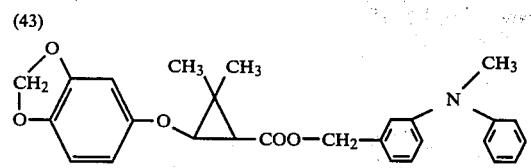

3'-(N-methylanilino)benzyl 2,2-dimethyl-3-(3,4-methylenedioxyphenoxy)cyclopropane carboxylate, $n^{20}_D$ 1.5981

(44) 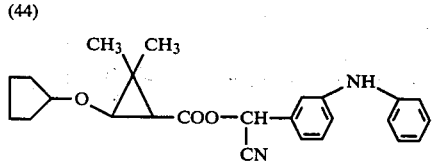

3'-anilino-α'-cyanobenzyl 2,2-dimethyl-3-cyclopentyloxycyclopropane carboxylate, $n^{20}_D$ 1.5853

(45) 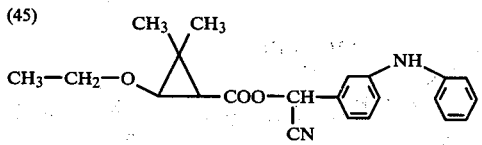

3'-anilino-α'-cyanobenzyl 2,2-dimethyl-3-ethoxycyclopropane carboxylate, $n^{20}_D$ 1.5787

(46) 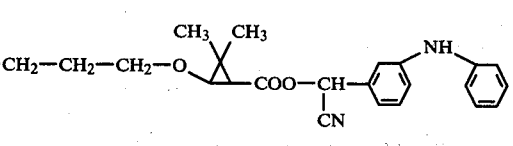

3'-anilino-α'-cyanobenzyl 2,2-dimethyl-3-(3-chloropropoxy) cyclopropane carboxylate, $n^{20}_D$ 1.5822

(47) 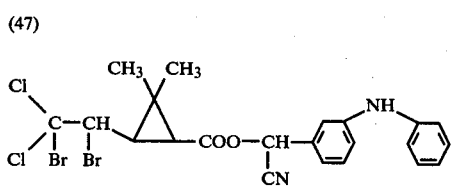

3'-anilino-α'-cyanobenzyl 2,2-dimethyl-3-(1,2-dibromo-2,2-dichloroethyl)cyclopropane carboxylate, $n^{20}_D$ 1.5878

(48) 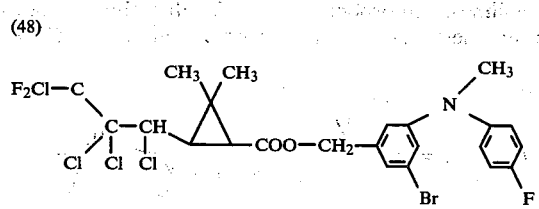

3'-(N-methyl-4-fluoroanilino)-5'-bromobenzyl 2,2-dimethyl-3-(1,2,2,3-tetrachloro-3,3-difluoropropyl) cyclopropane carboxylate, $n^{20}_D$ 1.5961

(49) 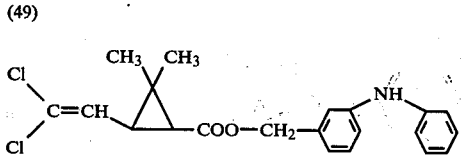

3'-anilinobenzyl 2,2-dimethyl-3-(2,2-dichlorovinyl)cyclopropane carboxylate, $n^{20}_D$ 1.5624

(50) 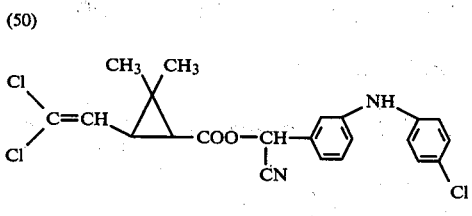

3'-(4-chloroanilino)-α'-cyanobenzyl 2,2-dimethyl-3-(2,2-dichlorovinyl)cyclopropane carboxylate, $n^{20}_D$ 1.5739

(51)
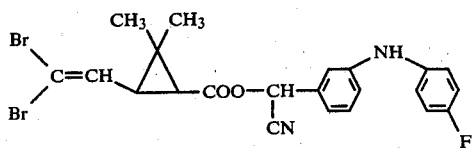

3'-(4-fluoroanilino)-α'-cyanobenzyl 2,2-dimethyl-3-(2,2-dibromovinyl)cyclopropane carboxylate, $n^{20}_D$ 1.5808

(52)
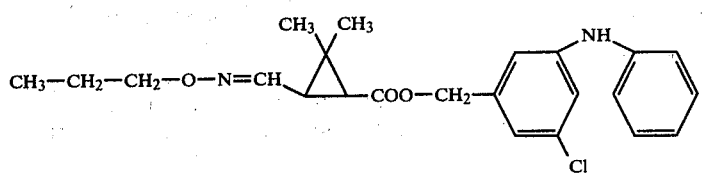

(53)
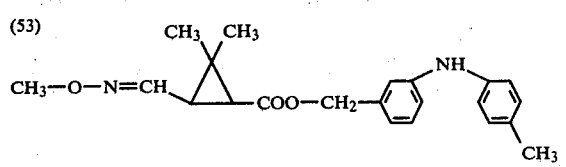

3'-(4-methylanilino)benzyl 2,2-dimethyl-3-methoxyiminomethylcyclopropane carboxylate, $n^{20}_D$ 1.5639

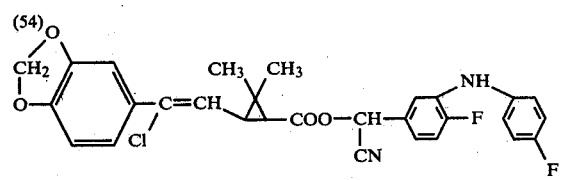

3'-(4-fluoroanilino)-4'-fluoro-α'-cyanobenzyl 2,2-dimethyl-3-[2-chloro-2-(3,4-methylenedioxyphenyl)-vinyl]cyclopropane carboxylate, $n^{20}_D$ 1.6004

(55)
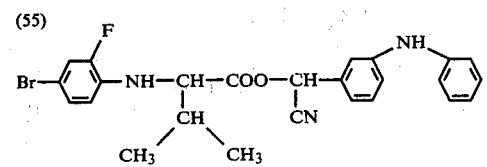

3'-anilino-α'-cyanobenzyl α-(2-fluoro-4-bromoanilino)isovalerate, $n^{20}_D$ 1.5982

(56)
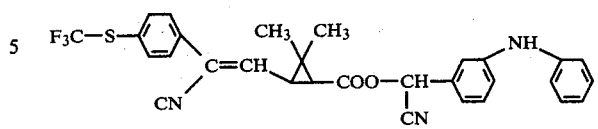

3'-anilino-α'-cyanobenzyl 2,2-dimethyl-3-[2-cyano-2-(4-trifluoromethylthiophenyl)vinyl]cyclopropane carboxylate, $n^{20}_D$ 1.5998

(57)
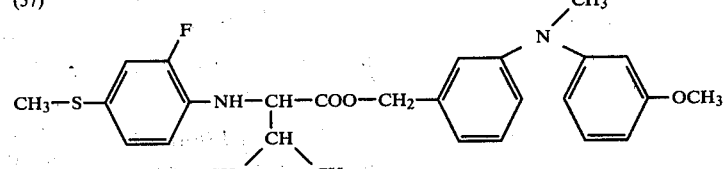

3'-(N-methyl-3-methoxyanilino)benzyl α-(2-fluoro-4-methylthioanilino)isovalerate, $n^{20}_D$ 1.5871

(58)
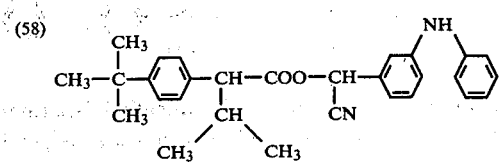

3'-anilino-α'-cyanobenzyl α-(4-tert.-butylphenyl)isovalerate, $n^{20}_D$ 1.5795

(59)
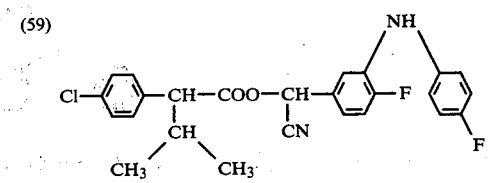

3'-(4-fluoroanilino)-4'-fluoro-α'-cyanobenzyl α-(4-chlorophenyl)isovalerate, $n^{20}_D$ 1.5770

(60)
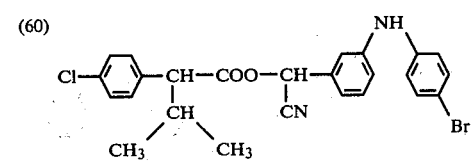

3'-(4-bromoanilino)-α'-cyanobenzyl α-(4-chlorophenyl)isovalerate, $n^{20}_D$ 1.5812

(61) 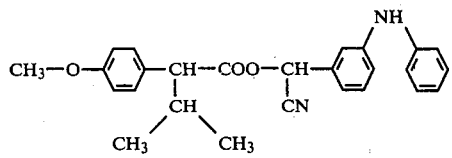

3'-anilino-α'-cyanobenzyl α-(4-methoxyphenyl)isovalerate, $n^{20}_D$ 1.5749

(62) 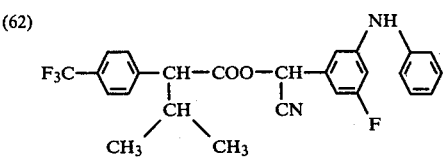

3'-anilino-5'-fluoro-α'-cyanobenzyl α-(4-trifluoromethylphenyl)isovalerate, $n^{20}_D$ 1.5763

(63) 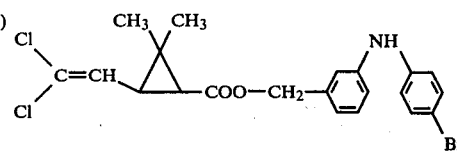

3'-(4-bromoanilino)benzyl 2,2-dimethyl-3-(2,2-dichlorovinyl)cyclopropane carboxylate, $n^{20}_D$ 1.5774

(64) 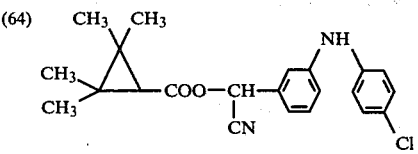

3'-(4-chloroanilino)-α'-cyanobenzyl 2,2,3,3-tetramethylcyclopropane carboxylate, $n^{20}_D$ 1.5648

(65) 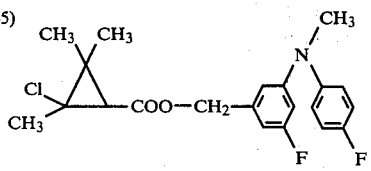

3'-(N-methyl-4-fluoroanilino)-5'-fluorobenzyl 2,2,3-trimethyl-3-chlorocyclopropane carboxylate, $n^{20}_D$ 1.5650

(66) 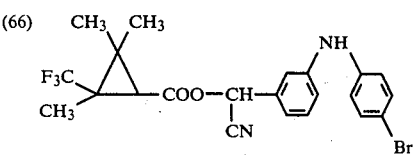

3'-(4-bromoanilino)-α'-cyanobenzyl 2,2,3-trimethyl-3-trifluoromethylcyclopropane carboxylate, $n^{20}_D$ 1.5681

(67) 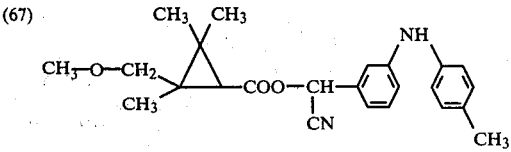

3'-(4-methylanilino)-α'-cyanobenzyl 2,2,3-trimethyl-3-methoxymethylcyclopropane carboxylate, $n^{20}_D$ 1.5702

(68) 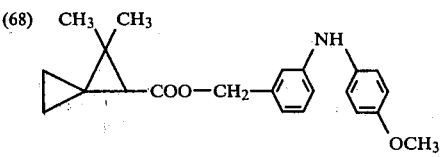

3'-(4-methoxyanilino)benzyl 2,2-dimethyl-3,3-ethylenecyclopropane carboxylate, $n^{20}_D$ 1.5645

(69) 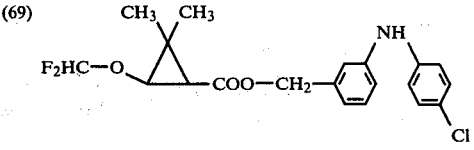

3'-(4-chloroanilino)benzyl 2,2-dimethyl-3-difluoromethoxycyclopropane carboxylate, $n^{20}_D$ 1.5739

(70) 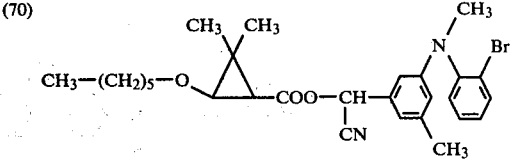

3'-(N-methyl-2-bromoanilino)-5'-methyl-α'-cyanobenzyl 2,2-dimethyl-3-n-hexyloxycyclopropane carboxylate, $n^{20}_D$ 1.5913

(71) 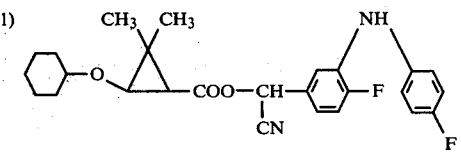

3'-(4-fluoroanilino)-4'-fluoro-α'-cyanobenzyl 2,2-dimethyl-3-cyclohexyloxycyclopropane carboxylate, $n^{20}_D$ 1.5890

(72) 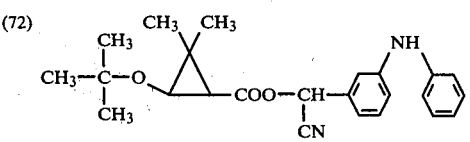

3'-anilino-α'-cyanobenzyl 2,2-dimethyl-3-tert.-butoxycyclopropane carboxylate, $n^{20}_D$ 1.5832

(73) 3'-(N-methylanilino)-α'-cyanobenzyl 2,2-dimethyl-3-(2,2-dichlorovinyl)cyclopropane carboxylate, $n^{20}_D$ 1.5728

(74) 3'-anilino-α'-cyanobenzyl α-(2-fluoro-4-trifluoromethylanilino)isovalerate, $n^{20}_D$ 1.5975

(75) 3'-(4-trifluoromethylanilino)-α'-cyanobenzyl 2,2-dimethyl-3-(2,2-dichlorovinyl)cyclopropane carboxylate, $n^{20}_D$ 1.5687

(76) 3'-(4-fluoroanilino)-α'-cyanobenzyl 2,2-dimethyl-3-(2,2-dichlorovinyl)cyclopropane carboxylate, $n^{20}_D$ 1.5706

(77) 3'-(4-chloroanilino)-α'-cyanobenzyl 2,2-dimethyl-3-(2,2-dibromovinyl)cyclopropane carboxylate, $n^{20}_D$ 1.5831

(78) 3'-(N-methylanilino)-α'-cyanobenzyl 2,2-dimethyl-3-(2,2-dibromovinyl)cyclopropane carboxylate, $n^{20}_D$ 1.5809

(79) 3'-(N-acetylanilino)-α'-cyanobenzyl 2,2-dimethyl-3-(2,2-dichlorovinyl)cyclopropane carboxylate, $n^{20}_D$ 1.5774

(80) 3'-(N-formylanilino)-α'-cyanobenzyl 2,2-dimethyl-3-(2,2-dimethylvinyl)cyclopropane carboxylate, $n^{20}_D$ 1.5717

(81) 3'-(4-trifluoromethylanilino)-α'-cyanobenzyl 2,2-dimethyl-3-(2-chloro-2-trifluoromethylvinyl)cyclopropane carboxylate, $n^{20}_D$ 1.5740

(82) 3'-(N-trifluoroacetylanilino)-α'-cyanobenzyl 2,2-dimethyl-3-(2-chloro-2-trifluoromethylvinyl)cyclopropane carboxylate, $n^{20}_D$ 1.5768

(83) 3'-(4-bromoanilino)-α'-cyanobenzyl α-(2,4-dichlorophenyl)isovalerate, $n^{20}_D$ 1.5852

(84) 3'-anilino-α'-cyanobenzyl α-(3-chlorophenyl)isovalerate, $n^{20}_D$ 1.5732

(85)
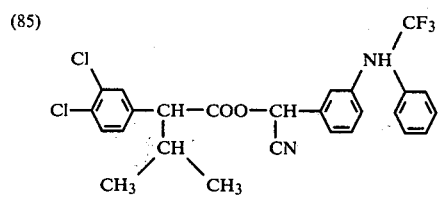

3'-(N-trifluoromethylanilino)-α'-cyanobenzyl α-(3,4-dichlorophenyl)isovalerate, $n^{20}_D$ 1.5790

(86)
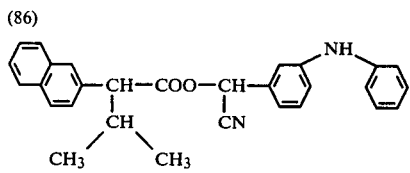

3'-anilino-α'-cyanobenzyl α-(2-naphthyl)isovalerate, $n^{20}_D$ 1.5875

(87)
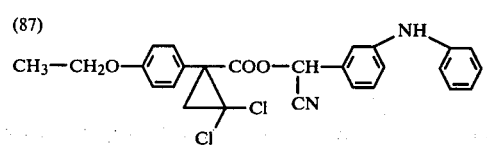

3'-anilino-α'-cyanobenzyl 1-(4-ethoxyphenyl)-2,2-dichlorocyclopropane carboxylate, $n^{20}_D$ 1.5851

(88)
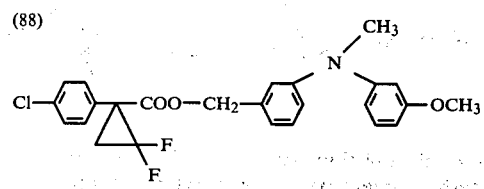

3'-(N-methyl-3-methoxyanilino)benzyl 1-(4-chlorophenyl)-2,2-difluorocyclopropane carboxylate, $n^{20}_D$ 1.5860

(89)
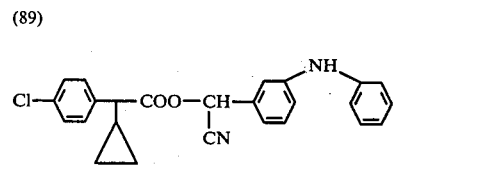

3'-anilino-α'-cyanobenzyl α-(4-chlorophenyl)-α-cyclopropylacetate, $n^{20}_D$ 1.5749

(90)
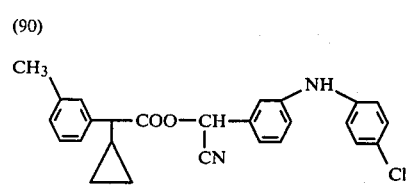

3'-(4-chloroanilino)-α'-cyanobenzyl α-(3-methylphenyl)-α-cyclopropylacetate, $n^{20}_D$ 1.5753

(91)
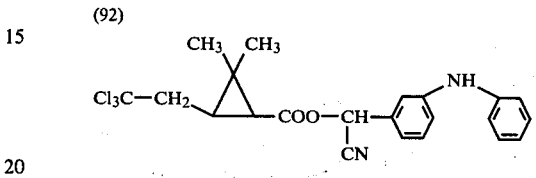

3'-(N-acetylanilino)-α'-cyanobenzyl α-(4-methoxyphenyl)-α-cyclopropylacetate, $n^{20}_D$ 1.5812

(92)
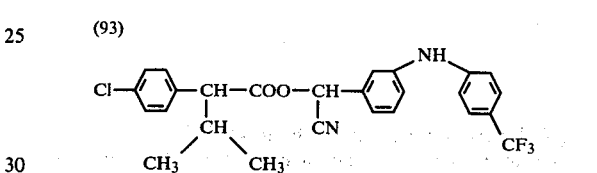

3'-anilino-α'-cyanobenzyl 2,2-dimethyl-3-(2,2,2-trichloroethyl)cyclopropane carboxylate, $n^{20}_D$ 1.5695

(93)
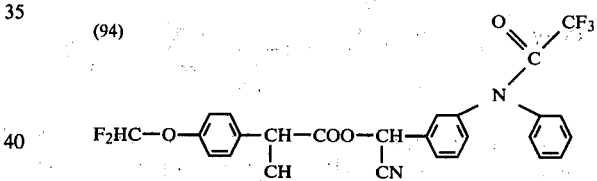

3'-(4-trifluoromethylanilino)-α'-cyanobenzyl α-(4-chlorophenyl)isovalerate, $n^{20}_D$ 1.5790

(94)
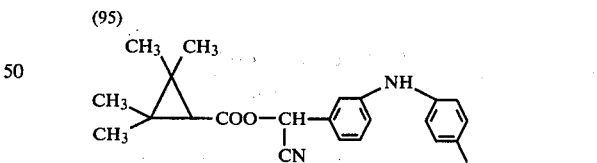

3'-(N-trifluoroacetylanilino)-α'-cyanobenzyl α-(4-difluoromethoxyphenyl)isovalerate, $n^{20}_D$ 1.5789

(95)
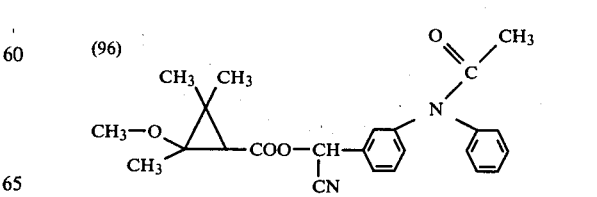

3'-(4-trifluoromethylanilino)-α'-cyanobenzyl 2,2,3,3-tetramethylcyclopropane carboxylate, $n^{20}_D$ 1.5631

(96)
3'-(N-acetylanilino)-α'-cyanobenzyl 2,2,3-trimethyl-3-methoxycyclopropane carboxylate, $n^{20}_D$ 1.5673

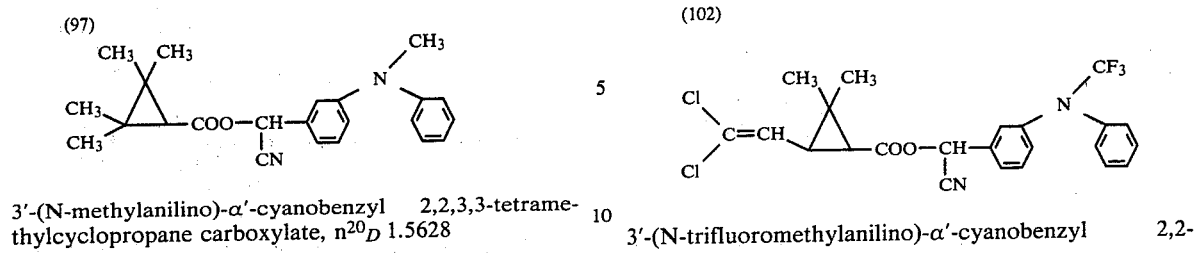

(97) 3'-(N-methylanilino)-α'-cyanobenzyl 2,2,3,3-tetramethylcyclopropane carboxylate, $n^{20}_D$ 1.5628

(102) 3'-(N-trifluoromethylanilino)-α'-cyanobenzyl 2,2-dimethyl-3-(2,2-dichlorovinyl)cyclopropane carboxylate, $n^{20}_D$ 1.5726

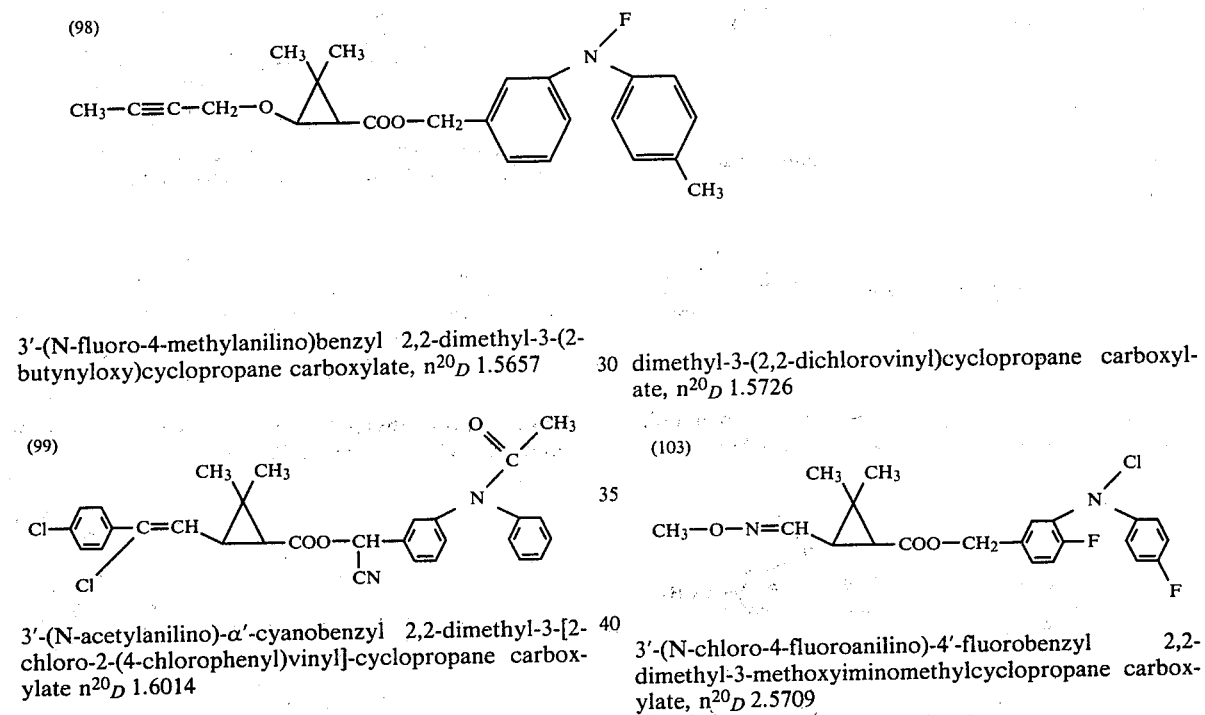

(98) 3'-(N-fluoro-4-methylanilino)benzyl 2,2-dimethyl-3-(2-butynyloxy)cyclopropane carboxylate, $n^{20}_D$ 1.5657

(99) 3'-(N-acetylanilino)-α'-cyanobenzyl 2,2-dimethyl-3-[2-chloro-2-(4-chlorophenyl)vinyl]-cyclopropane carboxylate $n^{20}_D$ 1.6014

(103) 3'-(N-chloro-4-fluoroanilino)-4'-fluorobenzyl 2,2-dimethyl-3-methoxyiminomethylcyclopropane carboxylate, $n^{20}_D$ 2.5709

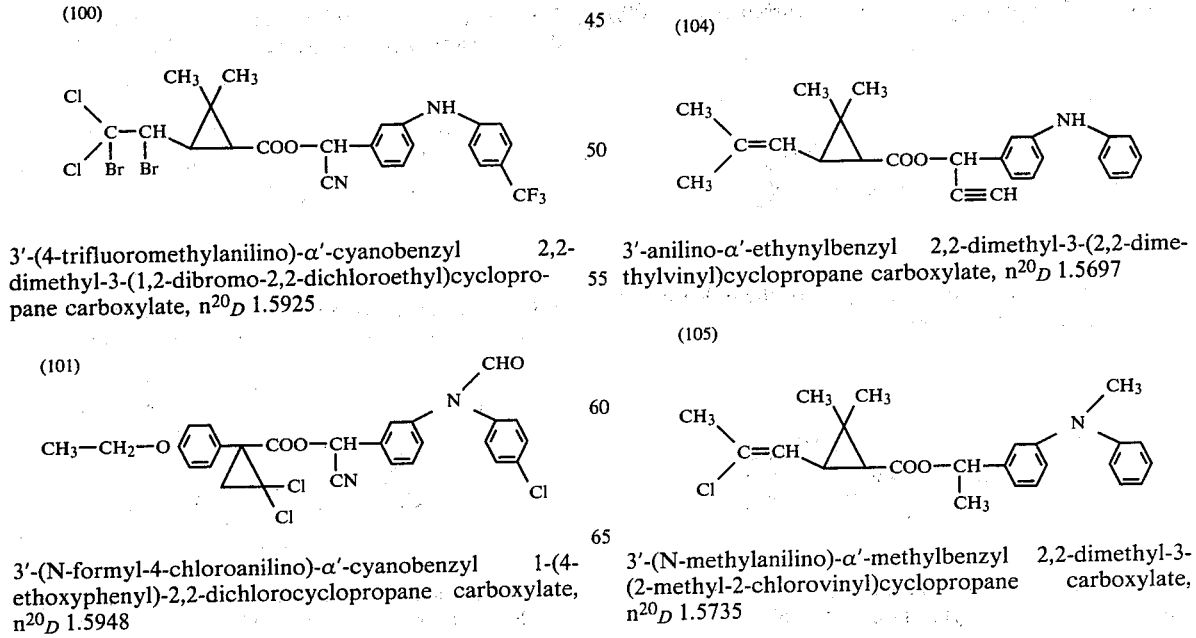

(100) 3'-(4-trifluoromethylanilino)-α'-cyanobenzyl 2,2-dimethyl-3-(1,2-dibromo-2,2-dichloroethyl)cyclopropane carboxylate, $n^{20}_D$ 1.5925

(104) 3'-anilino-α'-ethynylbenzyl 2,2-dimethyl-3-(2,2-dimethylvinyl)cyclopropane carboxylate, $n^{20}_D$ 1.5697

(101) 3'-(N-formyl-4-chloroanilino)-α'-cyanobenzyl 1-(4-ethoxyphenyl)-2,2-dichlorocyclopropane carboxylate, $n^{20}_D$ 1.5948

(105) 3'-(N-methylanilino)-α'-methylbenzyl 2,2-dimethyl-3-(2-methyl-2-chlorovinyl)cyclopropane carboxylate, $n^{20}_D$ 1.5735

(106)

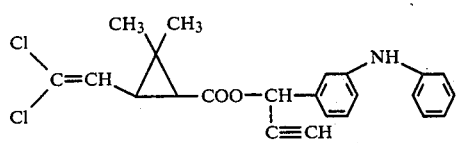

3'-anilino-α'-ethynylbenzyl 2,2-dimethyl-3-(2,2-dichlorovinyl)cyclopropane carboxylate, $n^{20}_D$ 1.5726

(107)

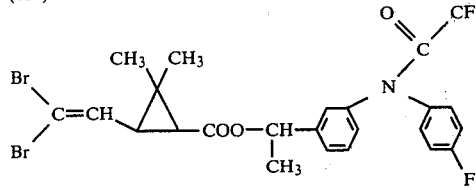

3'-(N-trifluoroacetyl-4-fluoroanilino)-α'-methylbenzyl 2,2-dimethyl-3-(2,2-dibromovinyl)cyclopropane carboxylate, $n^{20}_D$ 1.5934

(108)

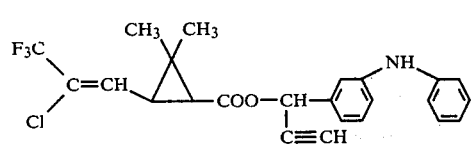

3'-anilino-α'-ethynylbenzyl 2,2-dimethyl-3-(2-chloro-2-trifluoromethylvinyl)cyclopropane carboxylate, $n^{20}_D$ 1.5802

(109)

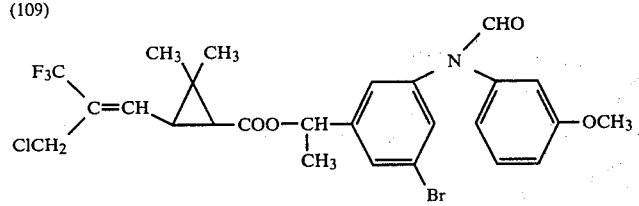

3'-(N-formyl-3-methoxyanilino)-5'-bromo-α'-methylbenzyl 2,2-dimethyl-3-(2-trifluoromethyl-2-chloromethylvinyl)cyclopropane carboxylate, $n^{20}_D$ 1.5985

(110)

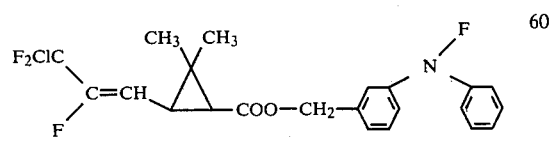

3'-(N-fluoroanilino)benzyl 2,2-dimethyl-3-(2-fluoro-2-chlorodifluoromethylvinyl)cyclopropane carboxylate, $n^{20}_D$ 1.5725

(111)

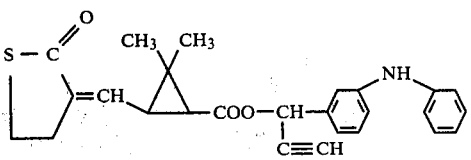

3'-anilino-α'-ethynylbenzyl 2,2-dimethyl-3-(2-oxothien-3-ylidenemethyl)cyclopropane carboxylate, $n^{20}_D$ 1.5783

(112)

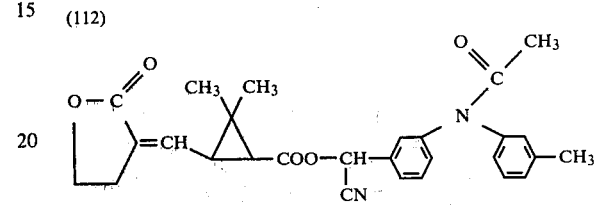

3'-(N-acetyl-3-methylanilino)-α'-cyanobenzyl 2,2-dimethyl-3-(2-oxooxolane-3-ylidenemethyl)cyclopropane carboxylate, $n^{20}_D$ 1.5814

(113)

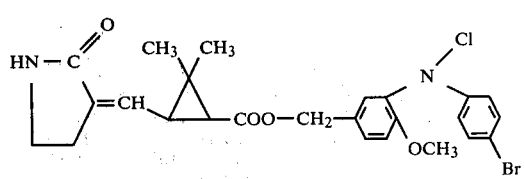

3'-(N-chloro-4-bromoanilino)-4'-methoxybenzyl 2,2-dimethyl-3-(2-oxopyrrolidine-3-ylidenemethyl)cyclopropane carboxylate, $n^{20}_D$ 1.5930

(114)

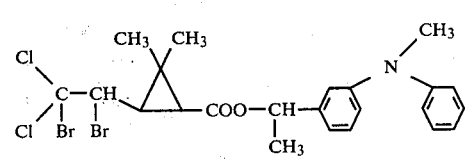

3'-(N-methylanilino)-α'-methylbenzyl 2,2-dimethyl-3-(1,2-dibromo-2,2-dichloroethyl)cyclopropane carboxylate, $n^{20}_D$ 1.5927

(115)

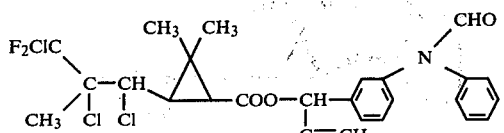

3'-(N-formylanilino)-α'-ethynylbenzyl 2,2-dimethyl-3-(1,2,3-trichloro-2-methyl-3,3-difluoropropyl)cyclopropane carboxylate, $n^{20}_D$ 1.5905

(116)

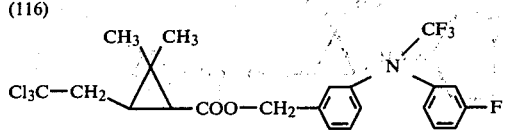

3'-(N-trifluoromethyl-4-fluoroanilino)benzyl 2,2-dimethyl-3-(2,2,2-trichloroethyl)cyclopropane carboxylate, $n^{20}_D$ 1.5782

(117)

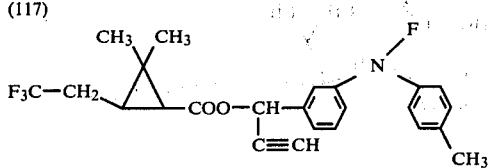

3'-(N-fluoro-4-methylanilino)-α'-ethynylbenzyl 2,2-dimethyl-3-(2,2,2-trifluoroethyl)cyclopropane carboxylate, $n^{20}_D$ 1.5726

(118)

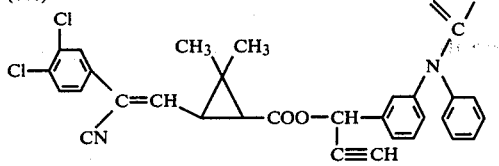

3'-(N-trifluoroacetylanilino)-α'-ethynylbenzyl 2,2-dimethyl-3-[2-cyano-2-(3,4-dichlorophenyl)vinyl]cyclopropane carboxylate, $n^{20}_D$ 1.5988

(119)

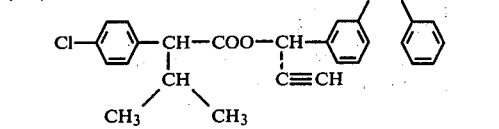

3'-anilino-α'-ethynylbenzyl α-(4-chlorophenyl)isovalerate, $n^{20}_D$ 1.5726

(120)

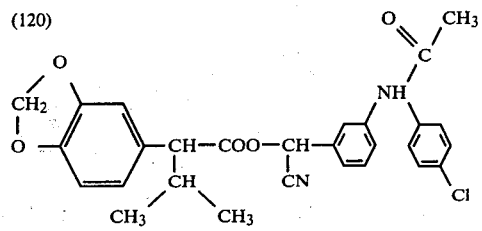

3'-(N-acetyl-4-chloroanilino)-α'-cyanobenzyl α-(3,4-methylenedioxyphenyl)isovalerate, $n^{20}_D$ 1.5861

(121)

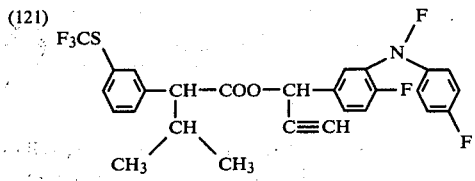

3'-(N-fluoro-4-fluoroanilino)-4'-fluoro-α'-ethynylbenzyl α-(3-trifluoromethylthiophenyl)isovalerate, $n^{20}_D$ 1.5885

(122)

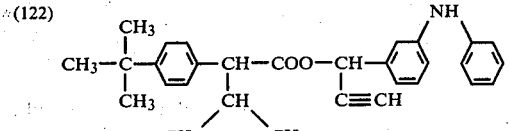

3'-anilino-α'-ethynylbenzyl α-(4-tert.-butylphenyl)isovalerate, $n^{20}_D$ 1.5802

(123)

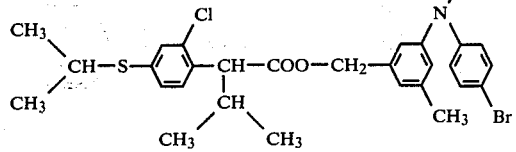

3'-(N-formyl-4-bromoanilino)-5'-methylbenzyl α-(2-chloro-4-isopropylthiophenyl)isovalerate, $n^{20}_D$ 1.6015

(124)

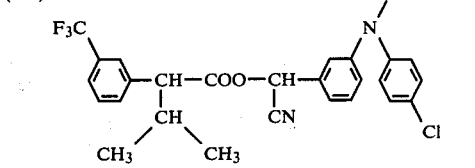

3'-(N-chloro-4-chloroanilino)-α'-cyanobenzyl α-(3-trifluoromethylphenyl)isovalerate, $n^{20}_D$ 1.5784

(125)
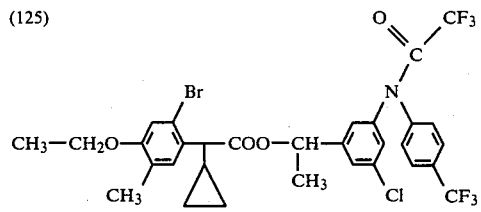

3'-(N-trifluoroacetyl-4-trifluoromethylanilino)-5'-chloro-α'-methylbenzyl α-(2-bromo-4-ethoxy-5-methylphenyl)-α-cyclopropylacetate, $n^{20}_D$ 1.6052

(126)
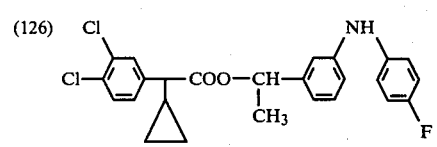

3'-(4-fluoroanilino)-α'-methylbenzyl α-(3,4-dichlorophenyl)-α-cyclopropylacetate, $n^{20}_D$ 1.5838

(127)
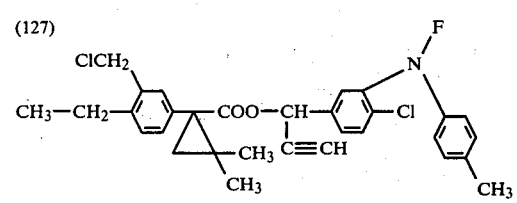

3'-(N-fluoro-4-methylanilino)-4'-chloro-α'-ethynylbenzyl 1-(3-chloromethyl-4-ethylphenyl)-2,2-dimethylcyclopropane carboxylate, $n^{20}_D$ 1.5961

(128)
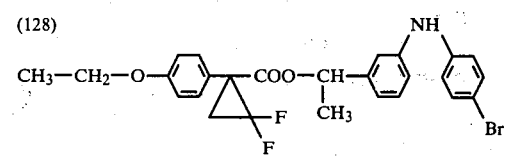

3'-(4-bromoanilino)-α'-methylbenzyl 1-(4-ethoxyphenyl)-2,2-difluorocyclopropane carboxylate, $n^{20}_D$ 1.5904

(129)
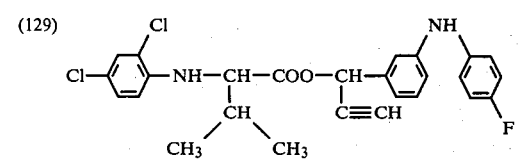

3'-(4-fluoroanilino)-α'-ethynylbenzyl α-(2,4-dichloroanilino)isovalerate, $n^{20}_D$ 1.5970

(130)
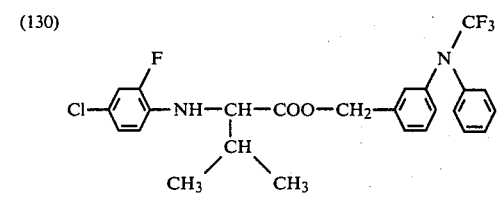

3'-(N-trifluoromethylanilino)benzyl α-(2-fluoro-4-chloroanilino)isovalerate, $n^{20}_D$ 1.5896

(131)
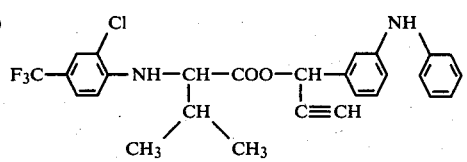

3'-anilino-α'-ethynylbenzyl α-(2-chloro-4-trifluoromethylanilino)isovalerate, $n^{20}_D$ 1.5981

(132)
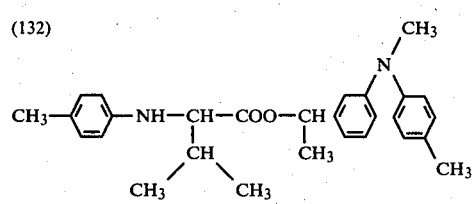

3'-(N-methyl-4-methylanilino)-α'-methylbenzyl α-(4-methylanilino)isovalerate, $n^{20}_D$ 1.5923

(133)
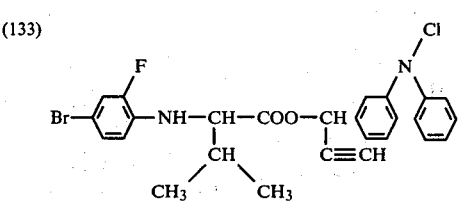

3'-(N-chloroanilino)-α'-ethynylbenzyl α-(2-fluoro-4-bromoanilino)isovalerate, $n^{20}_D$ 1.6007

(134)
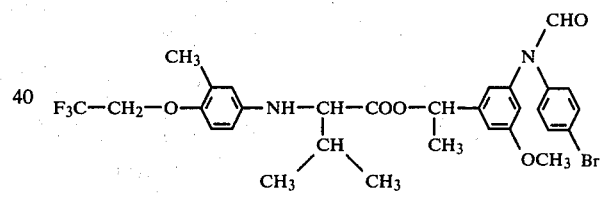

3'-(N-formyl-4-bromoanilino)-5'-methoxy-α'-methylbenzyl α-(3-methyl-4-trifluoroethoxyanilino)isovalerate, $n^{20}_D$ 1.6011

(135)
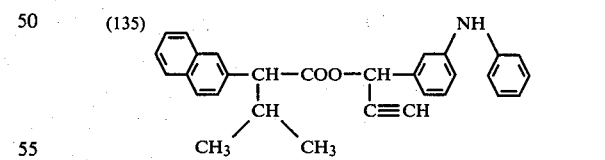

3'-anilino-α'-ethynylbenzyl α-(2-naphtyl)isovalerate, $n^{20}_D$ 1.5874

(136)
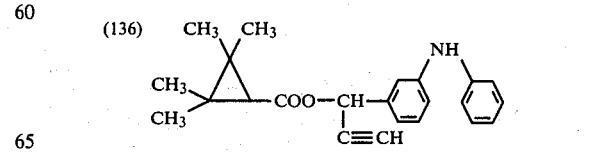

3'-anilino-α'-ethynylbenzyl 2,2,3,3-tetramethylcyclopropane carboxylate, $n^{20}_D$ 1.5607

(137) 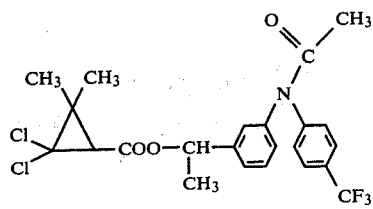

3'-(N-acetyl-4-trifluoromethylanilino)-α'-methylbenzyl 2,2-dimethyl-3,3-dichlorocyclopropane carboxylate $n^{20}_D$ 1.5780

(138) 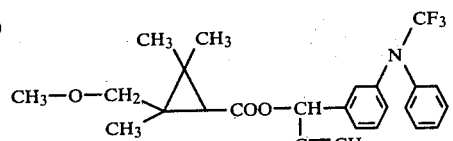

3'-(N-trifluoromethylanilino)-α'-ethynylbenzyl 2,2,3-trimethyl-3-methoxymethylcyclopropane carboxylate, $n^{20}_D$ 1.5729

(139) 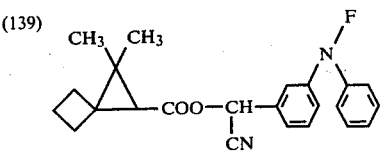

3'-(N-fluoroanilino)-α'-cyanobenzyl 2,2-dimethyl-3,3-trimethylenecyclopropane carboxylate, $n^{20}_D$ 1.5637

(140) 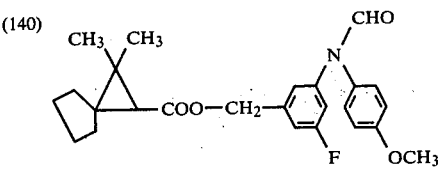

3'-(N-formyl-4-methoxyaniline)-5'-fluorobenzyl 2,2-dimethyl-3,3-tetramethylenecyclopropane carboxylate, $n^{20}_D$ 1.5764

(141) 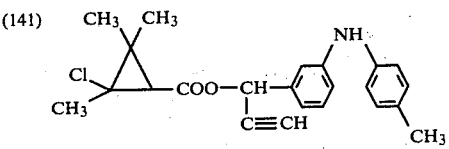

3'-(4-methylanilino)-α'-ethynylbenzyl 2,2,3-trimethyl-3-chlorocyclopropane carboxylate, $n^{20}_D$ 1.5713

(142) 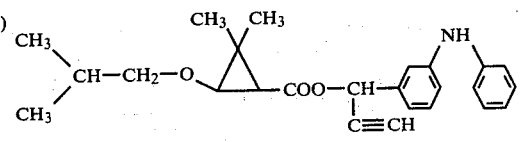

3'-anilino-α'-ethynylbenzyl 2,2-dimethyl-3-isobutoxycyclopropane carboxylate, $n^{20}_D$ 1.5862

(143) 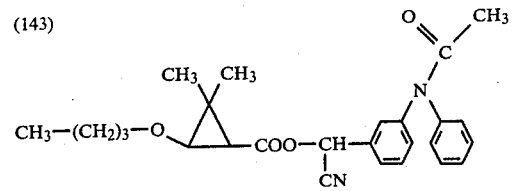

3'-(N-acetylanilino)-α'-cyanobenzyl 2,2-dimethyl-3-butoxycyclopropane carboxylate, $n^{20}_D$ 1.5897

(144) 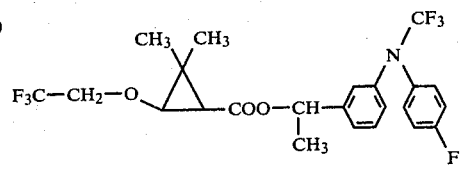

3'-(N-trifluoromethyl-4-fluoroanilino)-α'-methylbenzyl 2,2-dimethyl-3-trifluoroethoxycyclopropane carboxylate $n^{20}_D$ 1.5869

(145) 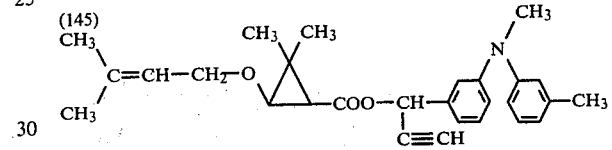

3'-(N-methyl-3-methylanilino)-α'-ethynylbenzyl 2,2-dimethyl-3-(3,3-dimethylallyloxy)cyclopropane carboxylate, $n^{20}_D$ 1.5891

(146) 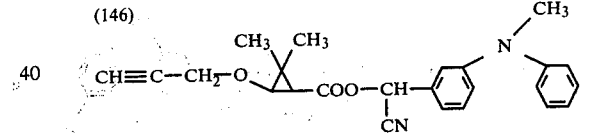

3'-(N-methylanilino)-α'-cyanobenzyl 2,2-dimethyl-3-(2-propynyloxy)cyclopropane carboxylate $n^{20}_D$ 1.5740

(147) 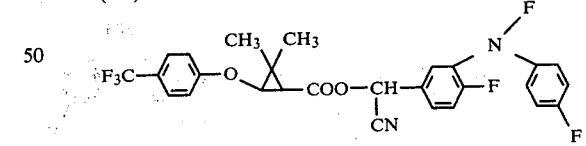

3'-(N-fluoro-4-fluoroanilino)-4'-fluoro-α'-cyanobenzyl 2,2-dimethyl-3-(4-trifluoromethylphenoxy)cyclopropane carboxylate, $n^{20}_D$ 1.5950

(148) 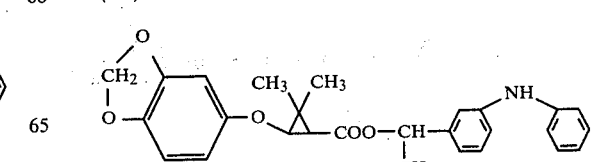

3′-anilino-α′-methylbenzyl 2,2-dimethyl-3-(3,4-methylenedioxyphenoxy)cyclopropane carboxylate, $n^{20}_D$ 1.5979

(149)
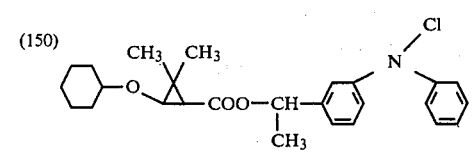

3′-(N-trifluoromethylanilino)-α′-cyanobenzyl 2,2-dimethyl-3-(3-chloropropoxy)cyclopropane carboxylate, $n^{20}_D$ 1.5906

(150)
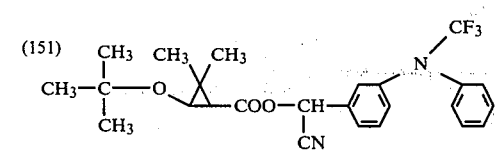

3′-(N-chloroanilino)-α′-methylbenzyl 2,2-dimethyl-3-cyclohexyloxycyclopropane carboxylate, $n^{20}_D$ 1.5912

(151)
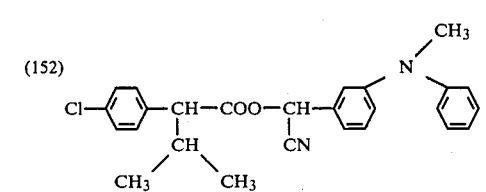

3′-(N-trifluoromethylanilino)-α′-cyanobenzyl 2,2-dimethyl-3-tert.-butoxycyclopropane carboxylate, $n^{20}_D$ 1.5873

(152)
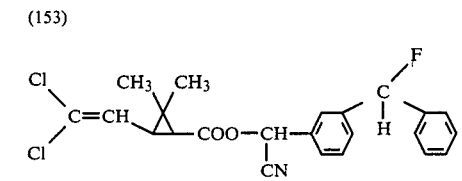

3′-(N-methylanilino)-α′-cyanobenzyl α-(4-chlorophenyl)isovalerate, $n^{20}_D$ 1.5827

(153)

3′-(α-fluorobenzyl)-α′-cyanobenzyl 2,2-dimethyl-3-(2,2-dichlorovinyl)cyclopropane carboxylate, $n^{20}_D$ 1.5523

(154)
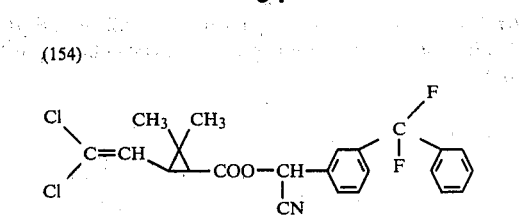

3′-(α,α-difluorobenzyl)-α′-cyanobenzyl 2,2-dimethyl-3-(2,2-dichlorovinyl)cyclopropane carboxylate, $n^{20}_D$ 1.5507

(155)
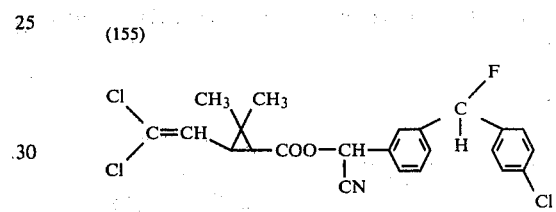

3′-(α-fluoro-4-chlorobenzyl)-α′-cyanobenzyl 2,2-dimethyl-3-(2,2-dichlorovinyl)cyclopropane carboxylate, $n^{20}_D$ 1.5576

(156)
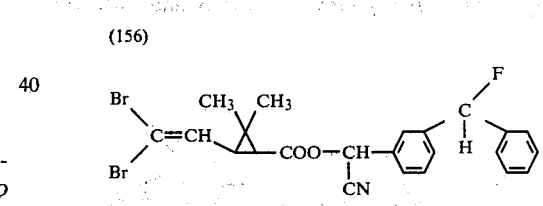

3′-(α-fluorobenzyl)-α′-cyanobenzyl 2,2-dimethyl-3-(2,2-dibromovinyl)cyclopropane carboxylate $n^{20}_D$ 1.5643

(157)
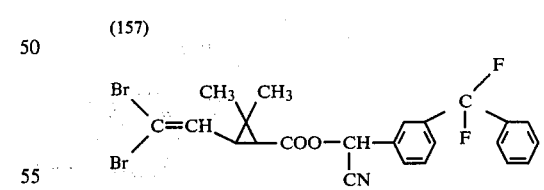

3′-(α,α-difluorobenzyl)-α′-cyanobenzyl 2,2-dimethyl-3-(2,2-dibromovinyl)cyclopropane carboxylate, $n^{20}_D$ 1.5667

(158)
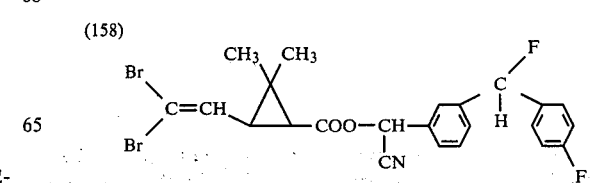

3'-(α,4-difluorobenzyl)-α'-cyanobenzyl 2,2-dimethyl-3-(2,2-dibromovinyl)cyclopropane carboxylate, $n^{20}_D$ 1.5615

(159)
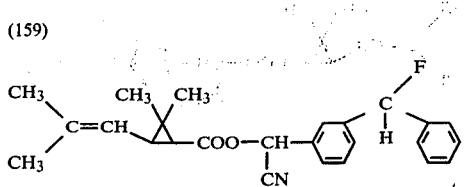

3'-(α-fluorobenzyl)-α'-cyanobenzyl 2,2-dimethyl-3-(2,2-dimethylvinyl)cyclopropane carboxylate, $n^{20}_D$ 1.5508

(160)
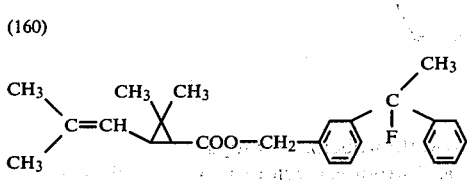

3'-(α-fluoro-α-methylbenzyl)benzyl 2,2-dimethyl-3-(2,2-dimethylvinyl)-cyclopropane carboxylate, $n^{20}_D$ 1.5486

(161)
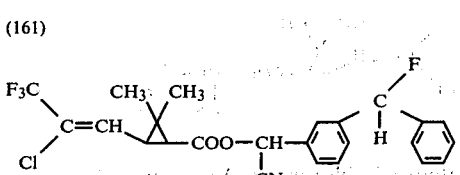

3'-(α-fluorobenzyl)-α'-cyanobenzyl 2,2-dimethyl-3-(2-chloro-2-trifluoromethylvinyl) cyclopropane carboxylate, $n^{20}_D$ 1.5530

(162)
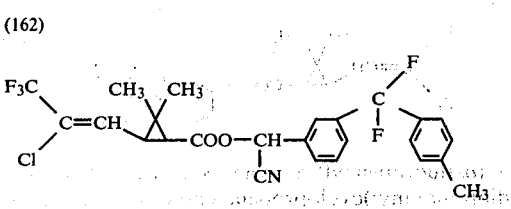

(163)
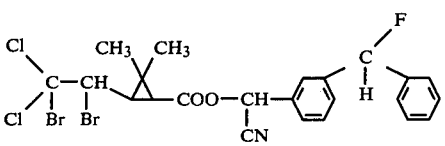

3'-(α-fluorobenzyl)-α'-cyanobenzyl 2,2-dimethyl-3-(1,2-dibromo-2,2-dichloroethyl)-cyclopropane carboxylate, $n^{20}_D$ 1.5684

(164)
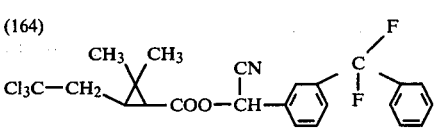

3'-(α,α-difluorobenzyl)-α'-cyanobenzyl 2,2-dimethyl-3-(2,2,2-trichloroethyl) cyclopropane carboxylate, $n^{20}_D$ 1.5575

(165)
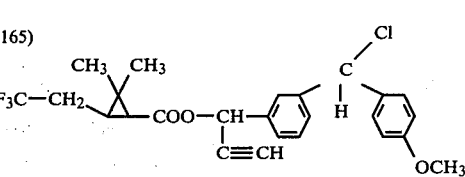

3'-(α-chloro-4-methoxybenzyl)-α'-ethynyl benzyl 2,2-dimethyl-3-(2,2,2-trifluoroethyl)cyclopropane carboxylate, $n^{20}_D$ 1.5498

(166)
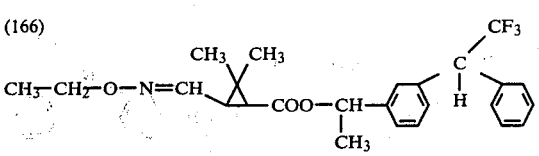

3'-(α-trifluoromethylbenzyl)-α'-methylbenzyl 2,2-dimethyl-3-ethoxyiminomethyl cyclopropane carboxylate, $n^{20}_D$ 1.5529

(167)
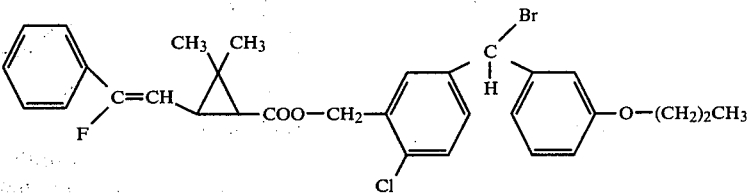

3'-(α,α-difluoro-4-methylbenzyl)-α'-cyanobenzyl 2,2-dimethyl-3-(2-chloro-2-trifluoromethylvinyl) cyclopropane carboxylate, $n^{20}_D$ 1.5547

3'-(α-bromo-3-propoxybenzyl)-6'-chlorobenzyl 2,2-dimethyl-3-(2-fluoro-2-phenylvinyl) cyclopropane carboxylate, $n^{20}_D$ 1.5869

(168)

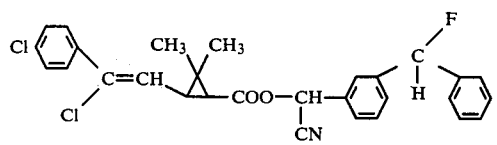

3'-(α-fluorobenzyl)-α'-cyanobenzyl 2,2-dimethyl-3-[2-chloro-2-(4-chlorophenyl)vinyl]cyclopropane carboxylate, $n^{20}_D$ 1.5784

(169)

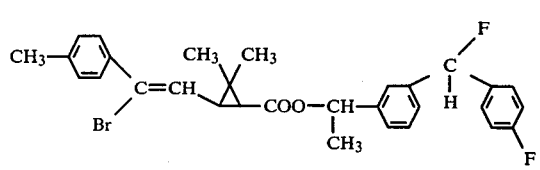

3'-(α,4-difluorobenzyl)-4'-fluoro-α'-methylbenzyl 2,2-dimethyl-3-[2-bromo-2-(4-methylphenyl)vinyl]cyclopropane carboxylate, $n^{20}_D$ 1.5822

(170)

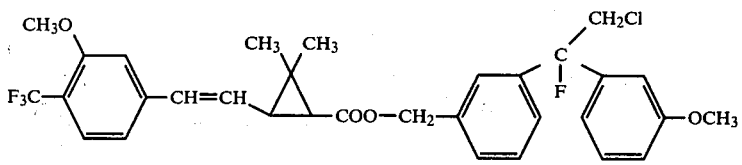

3'-(α-fluoro-α-chloromethyl-3-methoxybenzyl)benzyl 2,2-dimethyl-3-[2-(3-methoxy-4-trifluoromethylphenyl)vinyl]cyclopropane carboxylate, $n^{20}_D$ 1.5890

(171)

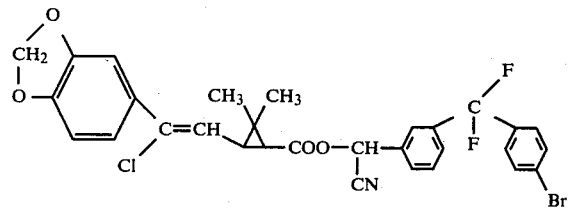

3'-(α,α-difluoro-4-bromobenzyl)-α'-cyanobenzyl 2,2-dimethyl-3-[2-chloro-2-(3,4-methylenedioxyphenyl)vinyl]cyclopropane carboxylate, $n^{20}_D$ 1.5966

(172)

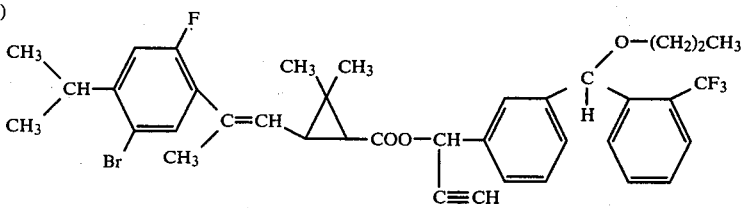

3'-(α-propoxy-2-trifluoromethylbenzyl)-5'-methyl-α'-ethynylbenzyl 2,2-dimethyl-3-[2-methyl-2-(2-fluoro-4-isopropyl-5-bromophenyl)vinyl]cyclopropane carboxylate, $n^{20}_D$ 1.6003

(173)

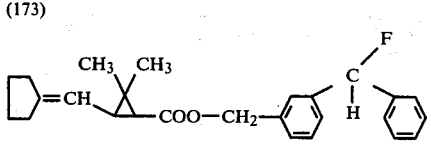

3'-(α-fluorobenzyl)benzyl 2,2-dimethyl-3-cyclopentylidenemethylcyclopropane carboxylate, $n^{20}_D$ 1.5579

(174)

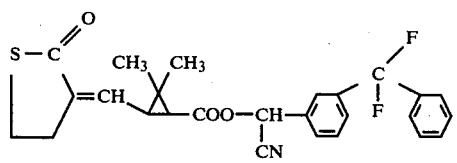

3'-(α,α-difluorobenzyl)-α'-cyanobenzyl 2,2-dimethyl-3-(2-oxothien-3-ylidenemethyl)cyclopropane carboxylate, $n^{20}_D$ 1.5768

(175)

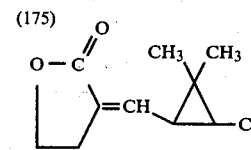

3'-[α-(1-chloro-2,2-difluoroethyl)-3-chlorobenzyl]-5'-bromo-α'-methylbenzyl 2,2-dimethyl-3-(2-oxooxolane-3-ylidenemethyl) cyclopropane carboxylate, $n^{20}_D$ 1.5990

(176)
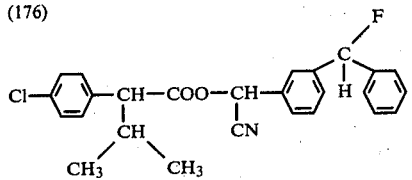
3'-(α-fluorobenzyl)-α'-cyanobenzyl α-(4-chlorophenyl)isovalerate, $n^{20}D$ 1.5664

(177)
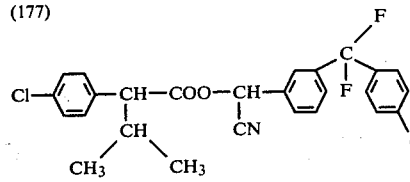
3'-(α,α-difluoro-4-chlorobenzyl)-α'-cyanobenzyl α-(4-chlorophenyl)isovalerate, $n^{20}_D$ 1.5719

(178)
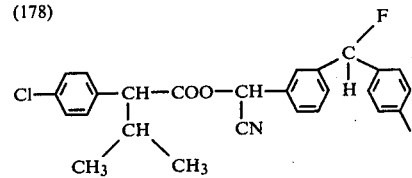
3'-(α,4-difluorobenzyl)-α'-cyanobenzyl α-(4-chlorophenyl)isovalerate, $n^{20}_D$ 1.5680

(179)
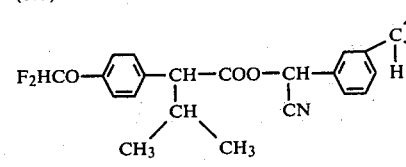
3'-(α-fluorobenzyl)-α'-cyanobenzyl α-(4-difluoromethoxyphenyl)isovalerate, $n^{20}_D$ 1.5705

(180)
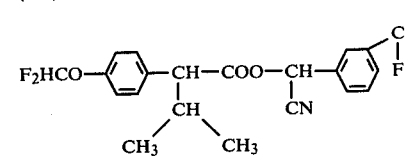
3'-α,α-difluoro-4-bromobenzyl)-α'-cyanobenzyl α-(4-difluoromethoxyphenyl)isovalerate, $n^{20}_D$ 1.5788

(181)
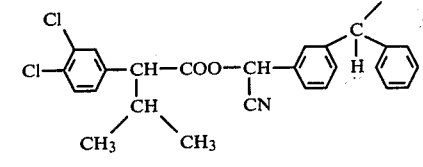
3'-(α-fluorobenzyl)-α'-cyanobenzyl α-(3,4-dichlorophenyl)isovalerate, $n^{20}_D$ 1.5687

(182)
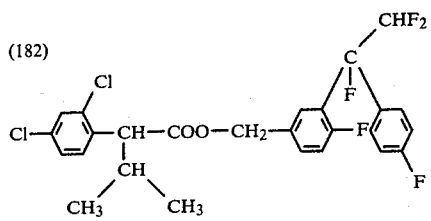
3'-(α-fluoro-α-difluoromethyl-4-fluorobenzyl)-4'-fluorobenzyl α-(2,4-dichlorophenyl)isovalerate, $n^{20}_D$ 1.5674

(183)
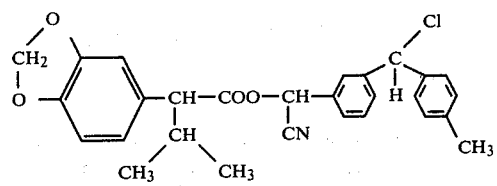
3'-(α-chloro-4-methylbenzyl)-α'-cyanobenzyl α-(3,4-methylenedioxyphenyl)isovalerate, $n^{20}_D$ 1.5805

(184)
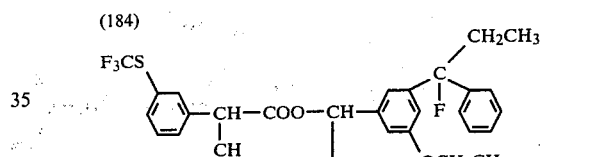
3'-(α-fluoro-α-ethylbenzyl)-5'-ethoxy-α'-ethynylbenzyl α-(3-trifluoromethylthiophenyl)isovalerate, $n^{20}_D$ 1.5873

(185)
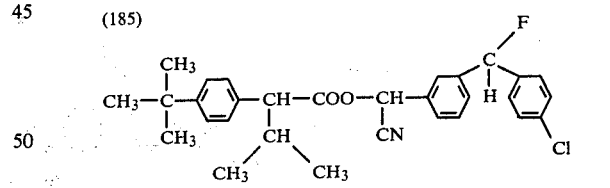
3'-(α-fluoro-4-chlorobenzyl)-α'-cyanobezyl α-(4-tert.-butylphenyl)isovalerate, $n^{20}_D$ 1.5794

(186)
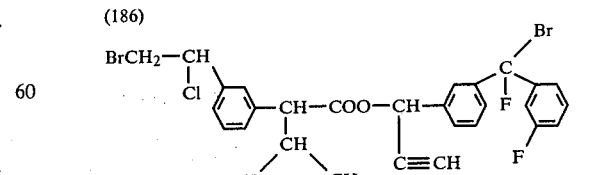
3'-(α-fluoro-α-bromo-3-fluorobenzyl)-α'-ethynylbenzyl α-[3-(1-chloro-2-bromoethyl)phenyl]isovalerate, $n^{20}_D$ 1.5912

(187)
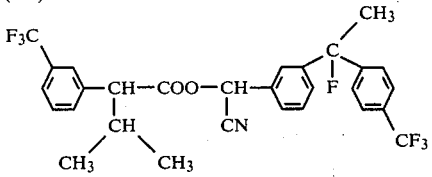

3′-(α-fluoro-α-methyl-4-trifluoromethylbenzyl)-α′-cyanobenzyl α-(3-trifluoromethylphenyl)isovalerate, $n^{20}_D$ 1.5790

(188)
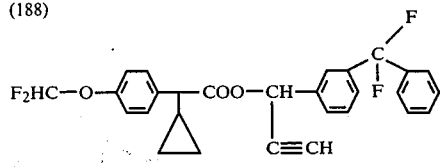

3′-(α,α-difluorobenzyl)-α′-ethynylbenzyl α-(4-difluoromethoxyphenyl)-α-cyclopropylacetate $n^{20}_D$ 1.5759

(189)
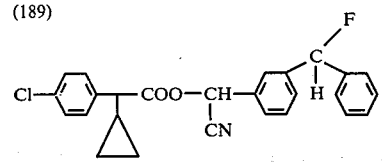

3′-(α-fluorobenzyl)-α′-cyanobenzyl α-(4-chlorophenyl)-α-cyclopropylacetate, $n^{20}_D$ 1.5728

(190)
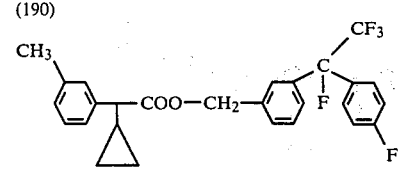

3′-(α,4-difluoro-α-trifluoromethylbenzyl)benzyl α-(3-methylphenyl)-α-cyclopropylacetate, $n^{20}_D$ 1.5792

(191)
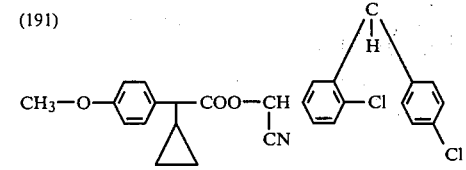

3′-(α,4-dichlorobenzyl)-4′-chloro-α′-cyanobenzyl α-(4-methoxyphenyl)-α-cyclopropylacetate, $n^{20}_D$ 1.5847

(192)
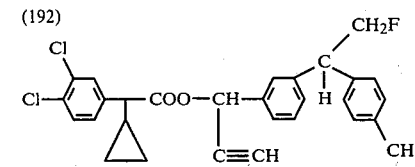

3′-(α-fluoromethyl-4-methylbenzyl)-α′-ethynylbenzyl α-(3,4-dichlorophenyl)-α-cyclopropylacetate, $n^{20}_D$ 1.5865

(193)
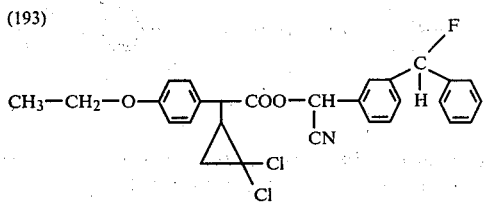

3′-(α-fluorobenzyl)-α′-cyanobenzyl 1-(4-ethoxyphenyl)-2,2-dichlorocyclopropane carboxylate, $n^{20}_D$ 1.5849

(194)
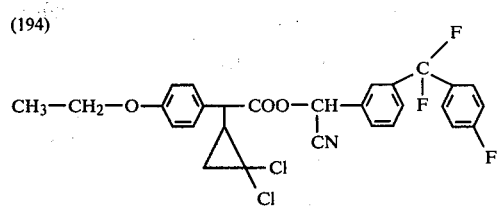

3′-(α,α,4-trifluorobenzyl)-α′-cyanobenzyl 1-(4-ethoxyphenyl)-2,2-dichlorocyclopropane carboxylate, $n^{20}_D$ 1.5836

(195)
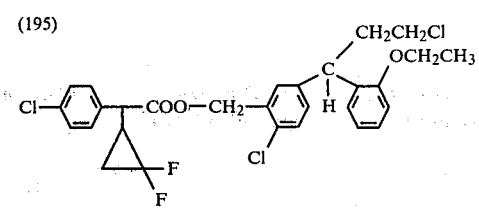

3′-(α-chloroethyl-2-ethoxybenzyl)-6′-chlorobenzyl 1-(4-chlorophenyl)-2,2-difluorocyclopropane carboxylate, $n^{20}_D$ 1.5980

(196)
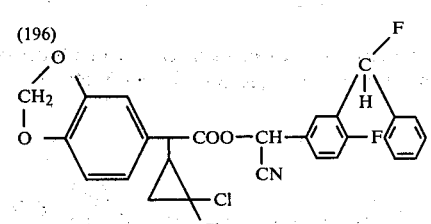

3′-(α-fluorobenzyl)-4′-fluoro-α′-cyanobenzyl 1-(3,4-methylenedioxyphenyl)-2,2-dichlorocyclopropane carboxylate, $n^{20}_D$ 1.5907

(197)
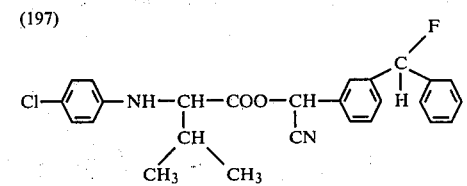

3′-(α-fluorobenzyl)-α′-cyanobenzyl α-(4-chloroanilino)isovalerate, $n^{20}_D$ 1.5676

(198) 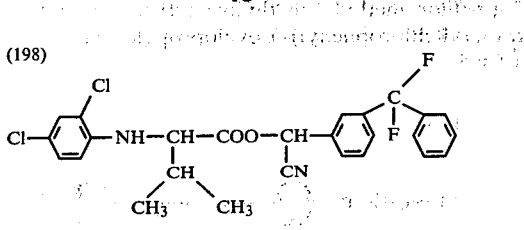

3'-(α,α-difluorobenzyl)-α'-cyanobenzyl α-(2,4-dichloroanilino)isovalerate, $n^{20}_D$ 1.5713

(199) 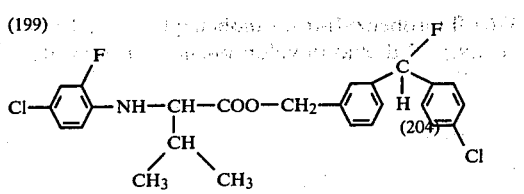

3'-(α-fluoro-4-chlorobenzyl)benzyl α-(2-fluoro-4-chloroanilino)isovalerate, $n^{20}_D$ 1.5745

(200) 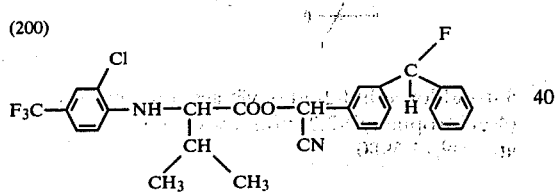

3'-(α-fluorobenzyl)-α'-cyanobenzyl α-(2-chloro-4-trifluoromethylanilino)isovalerate, $n^{20}_D$ 1.5769

(201) 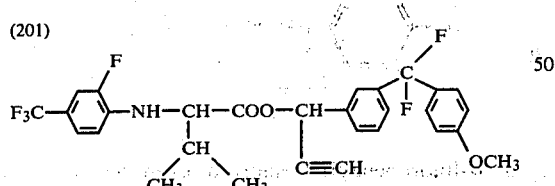

3'-(α,α-difluoro-4-methoxybenzyl)-α'-ethynylbenzyl α-(2-fluoro-4-trifluoromethylanilino)isovalerate, $n^{20}_D$ 1.5781

(202) 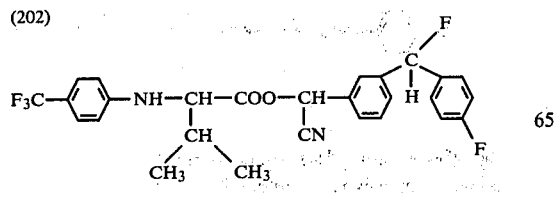

3'-(α,4-difluorobenzyl)-α'-cyanobenzyl α-(4-trifluoromethylanilino)isovalerate, $n^{20}_D$ 1.5698

(203) 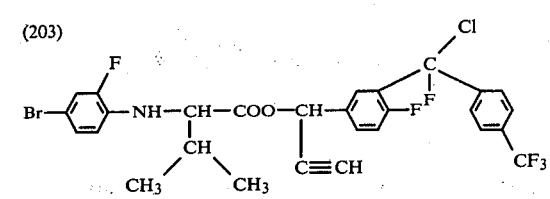

3'-(α-fluoro-α-chloro-4-trifluoromethylbenzyl)-4'-fluoro-α'-ethynylbenzyl α-(2-fluoro-4-bromoanilino)isovalerate, $n^{20}_D$ 1.5811

(204) 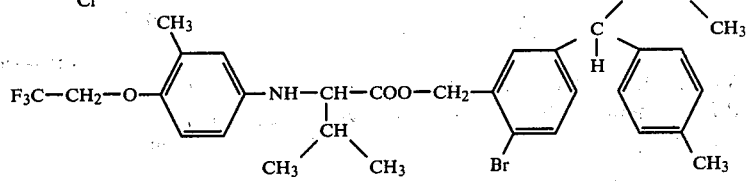

3'-(α-isopropoxy-4-methylbenzyl)-6'-bromobenzyl α-[3-methyl-4-(2,2,2-trifluoroethoxyanilino)]isovalerate, $n^{20}_D$ 1:6017

(205) 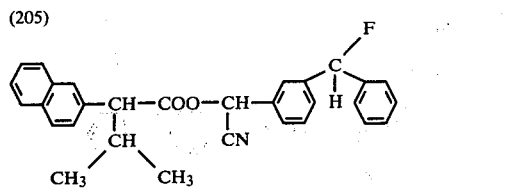

3'-(α-fluorobenzyl)-α'-cyanobenzyl α-(2-naphtyl)isovalerate, $n^{20}_D$ 1.5794

(206) 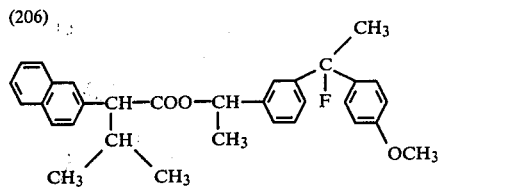

3'-(α-fluoro-α-methyl-4-methoxybenzyl)-α'-methylbenzyl α-(2-naphthyl)isovalerate, $n^{20}_D$ 1.5805

(207) 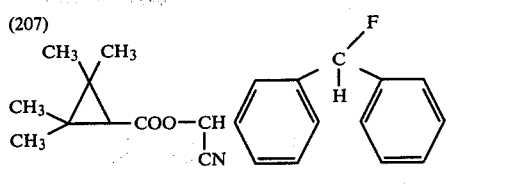

3'-(α-fluorobenzyl)-α'-cyanobenzyl 2,2,3,3-tetramethylcyclopropane carboxylate, $n^{20}_D$ 1.5618

(208)

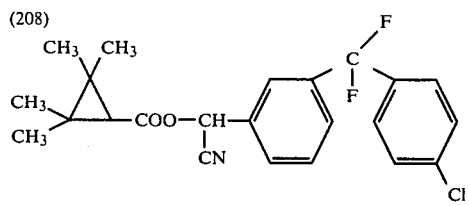

3'-(α,α-difluoro-4-chlorobenzyl)-α'-cyanobenzyl 2,2,3,3-tetramethylcyclopropane carboxylate, $n^{20}_D$ 1.5640

(209)

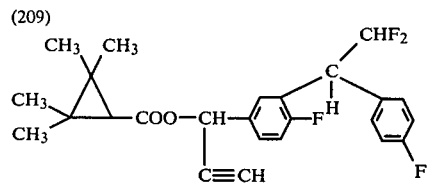

3'-(α-difluoromethyl-4-fluorobenzyl)-4'-fluoro-α'-ethynylbenzyl 2,2,3,3-tetramethylcyclopropane carboxylate, $n^{20}_D$ 1.5632

(210)

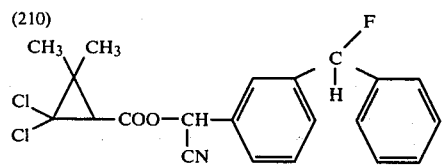

3'-(α-fluorobenzyl)-α'-cyanobenzyl 2,2-dimethyl-3,3-dichlorocyclopropane carboxylate, $n^{20}_D$ 1.5715

(211)

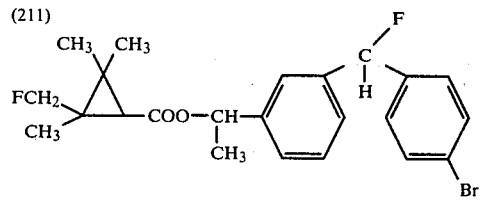

3'-(α-fluoro-4-bromobenzyl)-α'-methylbenzyl 2,2,3-trimethyl-3-fluoromethylcyclopropane carboxylate, $n^{20}_D$ 1.5748

(212)

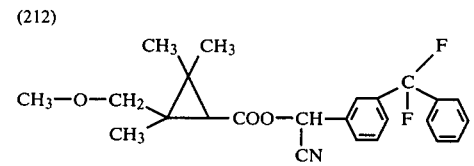

3'-(α,α-difluorobenzyl)-α'-cyanobenzyl 2,2,3-trimethyl-3-methoxymethylcyclopropane carboxylate, $n^{20}_D$ 1.5676

(213)

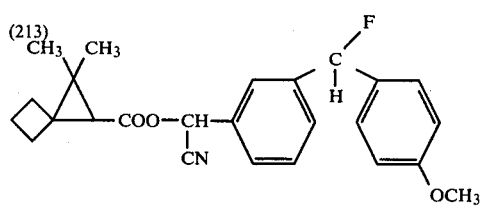

3'-(α-fluoro-4-methoxybenzyl)-α'-cyanobenzyl 2,2-dimethyl-3,3-trimethylenecyclopropane carboxylate, $n^{20}_D$ 1.5691

(214)

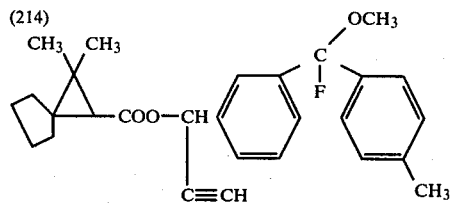

3'-(α-fluoro-α-methoxy-4-methylbenzyl)-α'-ethynylbenzyl 2,2-dimethyl-3,3-tetramethylenecyclopropane carboxylate, $n^{20}_D$ 1.5703

(215)

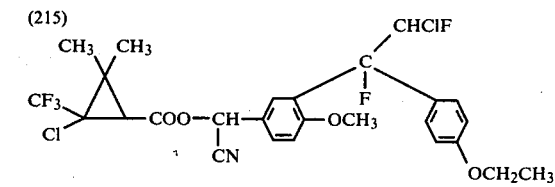

3'-(α-fluoro-α-chlorofluoromethyl-4-ethoxybenzyl)-4'-methoxy-α'-cyanobenzyl 2,2-dimethyl-3-chloro-3-trifluoromethlcyclopropane carboxylate, $n^{20}_D$ 1.5787

(216)

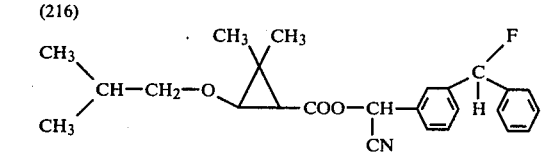

3'-(α-fluorobenzyl)-α'-cyanobenzyl 2,2-dimethyl-3-isobutoxycyclopropane carboxylate, $n^{20}_D$ 1.5790

(217)

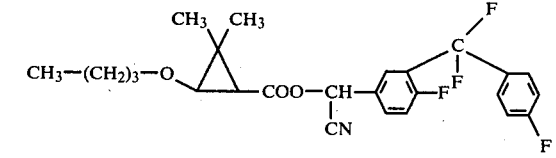

3'-(α,α,4-trifluorobenzyl)-4'-fluoro-α'-cyanobenzyl 2,2-dimethyl-3-butoxycyclopropane carboxylate, $n^{20}_D$ 1.5787

(218) 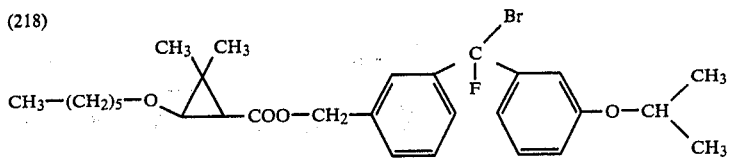

3'-(α-fluoro-α-bromo-3-isopropoxybenzyl)benzyl 2,2-dimethyl-3-hexyloxycyclopropane carboxylate, $n^{20}_D$ 1.5864

(219)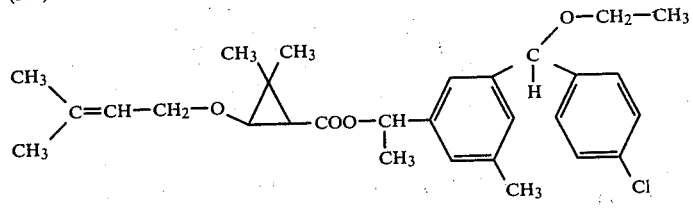

3'-(α-ethoxy-4-chlorobenzyl)-5'-methyl-α'-methylbenzyl 2,2-dimethyl-3-(3,3-dimethylallyloxy)cyclopropane carboxylate, $n^{20}_D$ 1.5823

(220) 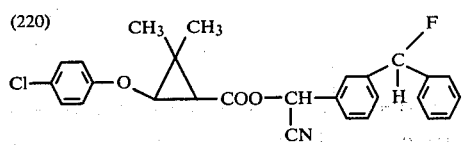

3'-(α-fluorobenzyl)-α'-cyanobenzyl 2,2-dimethyl-3-(4-chlorophenoxy)cyclopropane carboxylate, $n^{20}_D$ 1.5876

(221)

3'-(α,α-difluorobenzyl)-α'-cyanobenzyl 2,2-dimethyl-3-(4-methylphenoxy)cyclopropane carboxylate, $n^{20}_D$ 1.5837

(222) 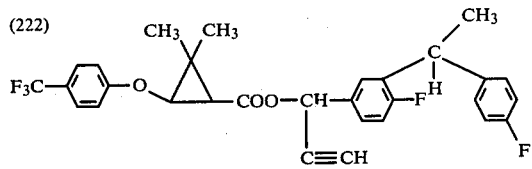

3'-(α-methyl-4-fluorobenzyl)-4'-fluoro-α'-ethynylbenzyl 2,2-dimethyl-3-(4-trifluoromethylphenoxy)cyclopropane carboxylate, $n^{20}_D$ 1.5855

(223) 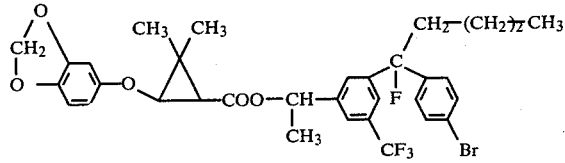

(224) 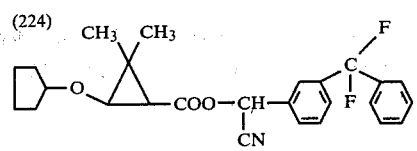

3'-(α,α-difluorobenzyl)-α'-cyanobenzyl 2,2-dimethyl-3-cyclopentyloxycyclopropane carboxylate, $n^{20}_D$ 1.5773

(225) 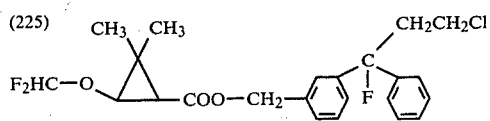

3'-(α'-chloroethyl-α-fluorobenzyl)benzyl 2,2-dimethyl-3-difluoromethoxycyclopropane carboxylate, $n^{20}_D$ 1.5673

(226) 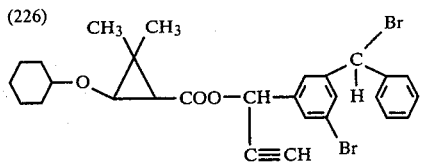

3'-(α-bromobenzyl)-5'-bromo-α'-ethynylbenzyl 2,2-dimethyl-3-cyclohexyloxycyclopropane carboxylate, $n^{20}_D$ 1.5894

(227)
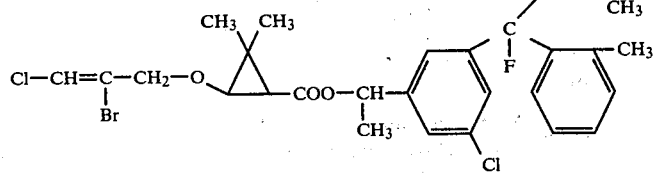

3'-(α-fluoro-α-isopropyl-2-methylbenzyl)-5'-chloro-α'-methylbenzyl 2,2-dimethyl-3-(2-bromo-3-chloroallyloxy)cyclopropane carboxylate, $n^{20}_D$ 1.5877

(228)
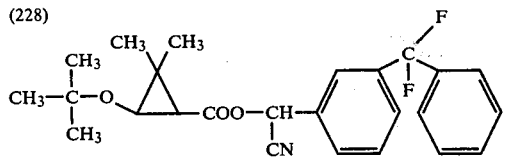

3'-(α,α-difluorobenzyl)-α'-cyanobenzyl 2,2-dimethyl-3-tert.-butoxycyclopropane carboxylate, $n^{20}_D$ 1.5762

(229)
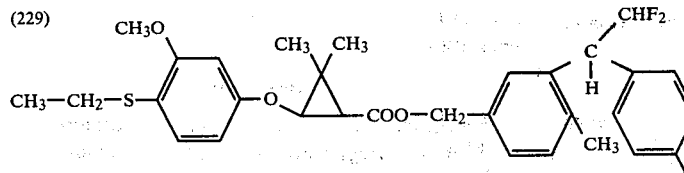

3'-(α-difluoromethyl-4-fluorobenzyl)-4'-methylbenzyl 2,2-dimethyl-3-(3-methoxy-4-ethylthiophenoxy)cyclopropane carboxylate, $n^{20}_D$ 1.5890

(230)
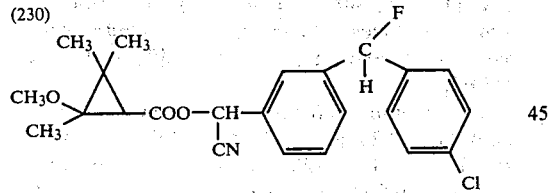

3'-(α-fluoro-4-chlorobenzyl)-α'-cyanobenzyl 2,2,3-trimethyl-3-methoxycyclopropane carboxylate, $n^{20}_D$ 1.5701

(231)

3'-(α-methoxy-2-fluorobenzyl)-6'-methoxybenzyl 2,2-dimethyl-3-(2,2,2-tribromoethyl)cyclopropane carboxylate, $n^{20}_D$ 1.5631

(232)
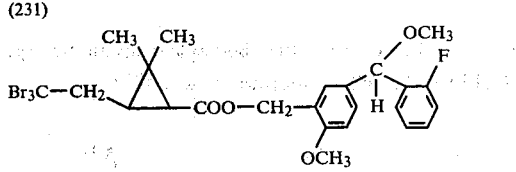

3'-(α,α-difluorobenzyl)benzyl 2,2-dimethyl-3-(2,2-dichlorovinyl)cyclopropane carboxylate, $n^{20}_D$ 1.5502

(233)
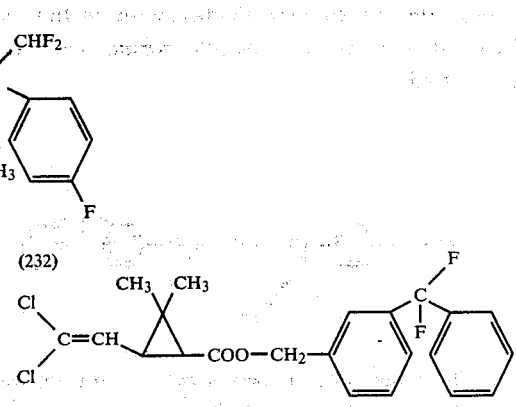

3'-(α-fluoro-4-bromobenzyl)-α'-ethynylbenzyl 2,2-dimethyl-3-(2-chloro-2-methylvinyl)cyclopropane carboxylate $n^{20}_D$ 1.5619

(234)
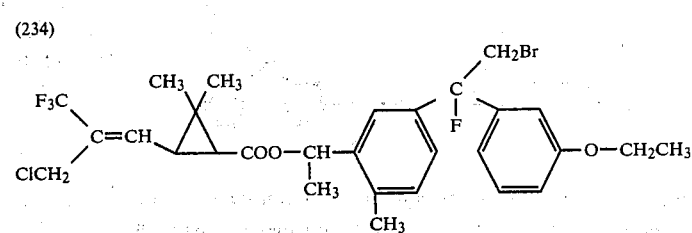

3'-(α-fluoro-α-bromomethyl-3-ethoxybenzyl)-6'-methyl-α'-methylbenzyl 2,2-dimethyl-3-(2-trifluoromethyl-2-chloromethylvinyl)cyclopropane carboxylate, $n^{20}_D$ 1.5670

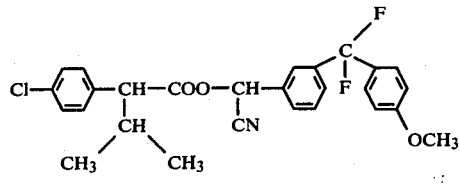
(235)

3'-(α,α-difluoro-4-methoxybenzyl)-α'-cyanobenzyl α-(4-chlorophenyl)isovalerate, $n^{20}_D$ 1.5731

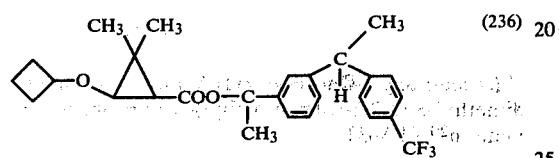
(236)

3'-(α-methyl-4-trifluoromethylbenzyl)-α'-methylbenzyl 2,2-dimethyl-3-cyclobutoxycyclopropane carboxylate, $n^{20}_D$ 1.5749

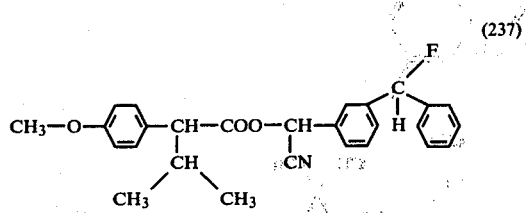
(237)

3'-(α-fluorobenzyl)-α'-cyanobenzyl α-(4-methoxyphenyl)isovalerate, $n^{20}_D$ 1.5650

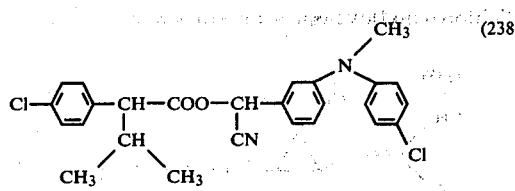
(238)

3'-(N-methyl-4-chloroanilino)-α'-cyanobenzyl α-(4-chlorophenyl)isovalerate, $n^{20}_D$ 1.5864

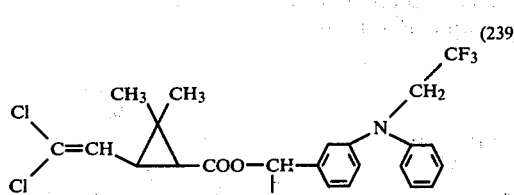
(239)

3'-[N-(2,2,2-trifluoroethyl)anilino]-α'-cyanobenzyl 2,2-dimethyl-3-(2,2-dichlorovinyl)cyclopropane carboxylate, $n^{20}_D$ 1.5703

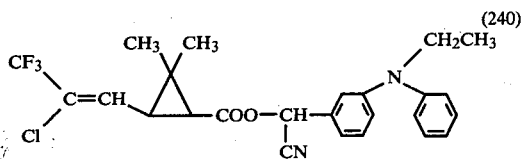
(240)

3'-(N-ethylanilino)-α'-cyanobenzyl 2,2-dimethyl-3-(2-chloro-2-trifluoromethylvinyl)cyclopropane carboxylate, $n^{20}_D$ 1.5716

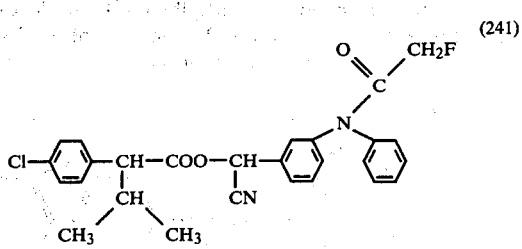
(241)

3'-(N-fluoroacetylanilino)-α'-cyanobenzyl α-(4-chlorophenyl)isovalerate, $n^{20}_D$ 1.5846

Next, typical synthesis examples will be described, but they are merely illustrative of the present invention and not intended for limiting the scope of the present invention.

Preparation 1

Synthesis of (1R, 3S) 2,2-dimethyl-3-(2,2-dichlorovinyl)cyclopropane carboxylic acid In accordance with the method described in Pestic. Sci. 1974. 5 791, 7.3 g of dl-cis-2,2-dimethyl-3-(2,2-dichlorovinyl)cyclopropane carboxylic acid dissolved in 100 ml of benzene was mixed at 50° C. with 4.2 g of l-α-methylbenzylamine dissolved in 15 ml of benzene and left at room temperature overnight. The obtained crystals were subjected to recrystallization from benzene three times to yield 3.0 g of l-α-methylbenzylamine salt of d-cis acid. [m.p. 147° C.; $[\alpha]^{20}_D$ −26.1° (C, 1.9 in EtOH]

To the amine salt thus obtained was added 25 ml of benzene and 25 ml of 3N HCl and the mixture was then shook well. The collected benzene layer was washed well and then the solvent was removed to yield 1.7 g of d-cis-, or (1R, 3S) 2.2-dimethyl-3-(2,2-dichlorovinyl)cyclopropane carboxylic acid. [m.p. 90° C.; $[\alpha]^{20}_D$ +27.2° (C, 2.1 in CHCl₃)]

Preparation 2

Synthesis of 3-anilino-α-cyanobenzylalcohol

In accordance with the method described in Zhur. Obshchei Khim 30, 2693 (1960), methyl 3-acetylaminobenzoate was reacted with iodo benzene in nitromethane in the presence of potassium carbonate and active copper powder to yield 3-anilinobenzoic acid and the intended product was obtained by the following steps.

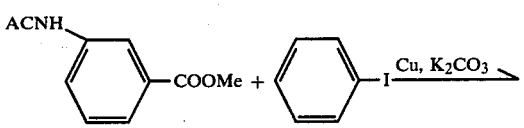

-continued

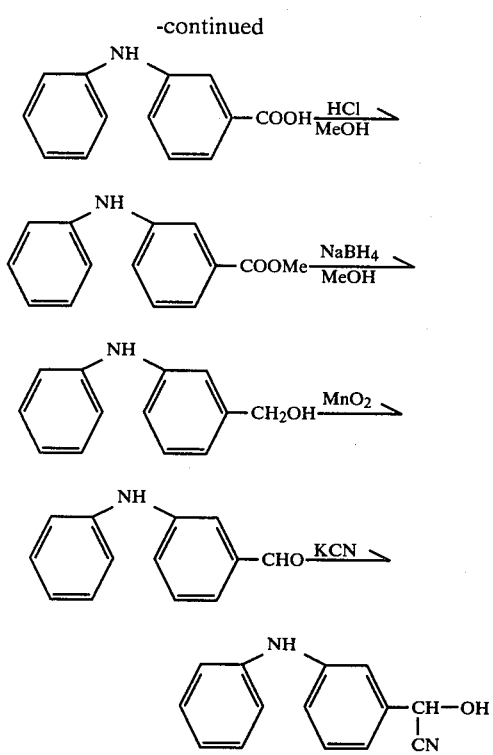

40 ml of 1N-HCl methanol solution was added to 4.2 g of 3-anilinobenzoic acid dissolved in 40 ml of methanol and then the reflux was carried out for 2 hours. After the removal of methanol, the ester obtained was extracted with ether. The ether layer was washed with 2% NaOH aqueous solution, and then with a saturated aqueous NaCl solution, to yield 4.2 g of methyl 3-anilinobenzoate. (m.p. 110°–112° C.)

Under cooling with ice water, 7.2 g of sodium borohydride was gradually dropped into 4.5 g of methyl 3-anilinobenzoate dissolved in 20 ml of methanol. Then, the temperature was gradually raised and the reflux was carried out for 8 hours. The reaction mixture was poured into 10% $H_2SO_4$ aqueous solution which was being cooled with ice. 5.0 g of oily substance was obtained after the extraction with ether. In order to remove the remaining unreacted methyl ester, the hydrolysis was carried out with the addition of 5% KOH. The by-produced 3-anilinobenzoic acid was removed through alkali-washing to yield 3.5 g of 3-anilinobenzylalcohol.

6.0 g of activated $MnO_2$ was added to 3.0 g of this 3-anilinobenzylalcohol dissolved in 30 ml of benzene and the reflux was carried out for 3 hours. The MnO produced was filtered off. The filtrate was condensed and passed through a column of 40 g silicagel to yield 2.7 g of 3-anilinobenzaldehyde.

1.5 g of KCN and 1.8 ml of acetic acid were added to 2.5 g of the aldehyde thus obtained dissolved 40 ml of ethanol and then left overnight under stirring. Then, the reaction mixture was poured into 100 ml of 2N-HCl and the extraction was effected with benzene. After washing with NaCl aqueous solution, the benzene layer was condensed to yield 2.7 g of 3-anilino-α-cyanobenzylalcohol.

The bromide as an alcohol reactive derivative was obtained by reacting the product thus obtained with thionylbromide in benzene in the presence of pyridine under cooling with ice.

Preparation 3

In accordance with the method described in Pestic. Sci. 1980, 11 188, 2.2 g of (1R, 4R, 5S)-4-hydroxy-6,6-dimethyl-3-oxabicyclo[3,1,0]hexa-2-one was reacted with 4.0 g of 3-anilino-α-cyanobenzylalcohol in the presence of toluene-4-sulfonic acid to yield lacton ether. The reaction mixture was subjected to column chromatography to isolate (S)-2-[(1R, 4R, 5S)-6,6-dimethyl-2-oxo-3-oxabicyclo[3,1,0]hexa-4-yloxy]-2-(3-anilinophenyl) acetonitrile, and 1.1 g of (S) 3-anilino-α-cyanobenzylalcohol was obtained by hydrolysis.

Preparation 4

(A) Ester synthesis by the reaction of alcohol with carboxylic acid chloride 4.5 g of 3-anilino-α-cyanobenzylalcohol dissolved in 20 ml of dried benzene was added to 4.8 g of (1R, 3S) 2,2-dimethyl-3-(2,2-dichlorovinyl)cyclopropane carboxylic acid chloride dissolved in 15 ml of dried benzene and further 3 ml of dried pyridine was added thereto as condensation accelerator to precipitate pyridine hydrochloride. The reaction mixture was allowed to be left in a tightly closed vessel at room temperature overnight and the crystals of pyridine hydrochloride were filtered off. The benzene solution was dried over sodium sulfate anhydride and benzene was removed under reduced pressure to yield 7.7 g of 3'-anilino-α'-cyanobenzyl (1R, 3S) 2,2-dimethyl-3-(2,2-dichlorovinyl)-cyclopropane carboxylate.

Preparation 5

(B) Ester synthesis by the reaction of alcohol with carboxylic acid 6.2 g of dicyclohexylcarbodiimide was added to the solution of 4.7 g of 2,2-dimethyl-3-(4-methylphenoxy)-cyclopropane carboxylic acid and 6.4 g of 3-(N-trifluoroacetylanilino)-α-cyanobenzyl alcohol dissolved in 50 ml of dried benzene and left in a tightly closed vessel overnight. Next day, the reflux was carried out under heating for 4 hours to complete the reaction and then dicyclohexyl urea precipitated after cooling was filtered off. An oily substance obtained by condensation of the filtrate was passed through a column of 100 g of silica gel to yield 8.6 g of 3'-(N-trifluoroacetylanilino)-α'-cyanobenzyl 2,2-dimethyl-3-(4-methylphenonoxy)-cyclopropane carboxylate.

Preparation 6

(C) Ester synthesis by the reaction of alcohol halide with alkali metal carboxylate 4.8 g of sodium 2,2-dimethyl-3-(2-oxooxolane-3-ylidenemethyl)cyclopropane carboxylate and 6.4 g of 3-(2-bromoanilino)-5-methylbenzyl chloride suspended in 50 ml of benzene was subjected to the reaction under 3 hour reflux in a stream of nitrogen gas. After cooling the reaction solution, sodium chloride precipitated was filtered off and the filtrate was washed well with the aqueous solution of NaCl and dried over sodium sulfate anhydride. Benzene was distilled off under reduced pressure to yield 8.3 g of 3'-(2-bromoanilino)-5'-methylbenzyl 2,2-dimethyl-3-(2-oxooxolane-3-ylidenemethyl) cyclopropane carboxylate.

Preparation 7

(D) Ester synthesis by the reaction of alcohol with lower alkyl carboxylate 4.5 g of methyl 2,2-dimethyl-3-(2,2,2-trifluoroethoxy)cyclopropane carboxylate and 6.1 g of 3-(α-trifluoromethyl-4-methylbenzyl)-α-ethynylbenzyl alcohol were heated up to 150° C. When the temperature reached 150° C., 0.25 g of sodium was added to the mixture and then methanol began to be distilled off. When the distillation of methanol ceased, 0.25 g of sodium was additionally added. These steps were repeated while the temperature was kept at around 150° C. until the theoretical amount of methanol was taken out. After cooling the reaction mixture, it was dissolved in ether and the ether solution was washed with dilute aqueous solution of HCl, the aqueous solution of sodium bicarbonate, NaCl aqueous solution and dried over sodium sulfate anhydride. Then, ether was distilled off under reduced pressure to yield 9.7 g of 3′-(α-trifluoromethyl-4-methylbenzyl)-α′-ethynylbenzyl 2,2-dimethyl-3-(2,2,2-trifluoroethoxy)cyclpropane carboxylate.

Preparation 8

(E) Ester synthesis by the reaction of alcohol with carboxylic acid anhydride 12.1 g of α-(3-methyl-4-trifluoroethoxyanilino)isovaleric acid anhydride and 6.5 g of 3-(N-methyl-4-bromoanilino)-5-methoxybenzyl alcohol were dissolved in 50 ml of dried pyridine and stirred at room temperature overnight. Next day, the reaction solution was poured into 100 g of ice water and extracted with 20 ml of ether three times. The collected ether layers were extracted twice with 20 ml of 5% aqueous solution of sodium hydroxide to remove the by-produced carboxylic acid. The ether solution was washed with the diluted aqueous solution of hydrochloric acid, the aqueous solution of sodium bicarbonate, and NaOH aqueous solution, and dried over sodium sulfate anhydride. Ether was removed under reduced pressure to yield a crude ester, which was passed through a column of 20 g of active alumina to yield 9.8 g of 3′-(N-methyl-4-bromoanilino)-5′-methoxybenzyl α-(3-methyl-4-trifluoroethoxyanilino)isovalerate.

Preparation 9

(F) Ester synthesis by the reaction of alcohol halide with carboxylate of organic tert. base 8.0 g of 3-(α-methoxy-3-bromobenzyl)-α-methylbenzylbromide was added to 5.4 g of α-(4-trifluoromethoxyphenyl)isovaleric acid dissolved in 50 ml of benzene. After 4 ml of triethylamine was added to it under stirring, the reaction was carried out at 60°–80° C. for 3 hours and then the reaction mixture was dissolved in ether. The ether solution was washed with a dilute aqueous solution of hydrochloric acid, an aqueous solution of sodium bicarbonate, and NaOH aqueous solution and then dried over sodium sulfate anhydride. Ether was distilled off under reduced pressure to yield 9.7 g of 3′-(α-methoxy-3-bromobenzyl)-α′-methylbenzyl α-(4-trifluoromethoxyphenyl) isovalerate.

Preparation 10

Synthesis of 3-(N-methylanilino)-α-cyanobenzyl alcohol ester

N-methyl derivative of anilinobenzyl alcohol ester was also prepared by reacting the ester with formaline in the presence of sodium cyanoborohydride.

6 ml of 35% of formaline and 1.0 g of sodium cyanoborohydride were added to 3.1 g of 3′-anilino-α′-cyanobenzyl 2,2,3,3-tetramethylcyclopropane carboxylate dissolved in 50 ml of acetanilide and stirred at room temperature overnight. After 50 ml of 2N-HCl was poured into the reaction solution to decompose excess sodium cyanoborohydride, the reaction solution was extracted with ether. The ether layer was thoroughly washed with saturated aqueous NaCl solution and then ether was distilled off to yield an oily substance. The oily substance was purified by column chromatography on silica gel to yield 2.7 g of 3′-(N-methylanilino)-α′-cyanobenzyl 2,2,3,3-tetramethylcyclopropane carboxylate.

Preparation 11

Synthesis of 3-(α-fluorobenzyl)-α-cyanobenzyl alcohol ester 3-(α-fluorobenzyl)-α-cyanobenzyl alcohol ester was synthesized by fluoridating the known 3-(α-hydroxybenzyl)-α-cyanobenzyl alcohol ester with 2-chloro-1,1,2-trifluoroethyldietheramine.

Under cooling with ice, 3.2 g of 2-chloro-1,1,2-trifluoroethyldiethylamine was added to 3′-(α-hydroxybenzyl)-α′-cyanobenzyl 2,2-dimethyl-3-methoxyiminomethylcyclopropane carboxylate and thereafter stirred for 2 hours. Then the reaction mixture was stirred at room temperature overnight. The reaction solution was washed with a dilute aqueous solution of hydrochloric acid, and a saturated aqueous NaCl solution and then condensed to yield an oily substance. The oily substance was passed over a column of 50 ml alumina to yield 2.9 g of 3′-(α-fluorobenzyl)-α′-cyanobenzyl 2,2-dimethyl-3-methoxyiminocyclopropane carboxylate.

The compounds listed in the below Table were prepared according to the methods similar to those in Preparation Nos. 4–11. In the Table, the indications "a, b, c, d, e, f and g" have the following meanings.

"a"—Esterification method by reaction between alcohol and carboxylic acid halide (Preparation 4)

"b"—Esterification method by dehydration between acid derivative of dicyclohexylcarboxyimide and alcohol in an inert solvent (Preparation 5)

"c"—Method by the reaction between alcohol halide and alkali metal-, silver- or organic tert. base-salt of acid (Preparations 6 and 9)

"d"—Transesterification method using alkali metal, alkali metal alkoxide or sodium hydride as catalyst (Preparation 7)

"e"—Method by the reaction between alcohol and carboxylic acid anhydride (Preparation 8)

"f"—Method by the alkylation of amino group in ester (Preparation 10)

"g"—Method by the fluoridation of hydroxy group or ketone group in ester

| Compound | R | —CH(R₁)—C₆H₃(R₂)—A—C₆H₄(R₂') | Esterification method | Yield (%) |
|---|---|---|---|---|
| 242 | (CH₃)₂C(Cl)=CH—cyclopropyl(CH₃)₂ | —CH₂—C₆H₄—N(CH₃)—C₆H₄—OCH₃ | f | 85 |
| 243 | 4-Cl-C₆H₄—CH(CH₃)—CH(CH₃)— | —CH(CN)—C₆H₄—NH—C₆H₄—Cl | e | 79 |
| 244 | cyclohexyl-O—cyclopropyl(CH₃)₂ | —CH(CN)—C₆H₃(F)—NH—C₆H₄—F | c | 83 |
| 245 | Br₃C—CH₂—cyclopropyl(CH₃)₂ | —CH₂—C₆H₄—N(CHO)—C₆H₅ | a | 88 |
| 246 | 4-CF₃-C₆H₄—NH—CH—CH(CH₃)₂ | —CH(CN)—C₆H₄—NH—C₆H₄—F | d | 82 |
| 247 | F₂HC—O—C₆H₄—cyclopropyl | —CH(C≡CH)—C₆H₄—NH—C₆H₅ | a | 90 |
| 248 | CF₃,CH₃-cyclopropyl(CH₃)₂ | —CH(CH₃)—C₆H₄—N(CF₃)—C₆H₅ | b | 85 |
| 249 | 4-Cl-C₆H₄—O—cyclopropyl(CH₃)₂ | —CH(C≡CH)—C₆H₄—NH—C₆H₄—Cl | d | 78 |
| 250 | cyclopentylidene=CH—cyclopropyl(CH₃)₂ | —CH(CH₃)—C₆H₄—N(CH₃)—C₆H₅ | e | 80 |
| 251 | C₆H₅—C(F)=CH—cyclopropyl(CH₃)₂ | —CH₂—C₆H₄—N(F)—C₆H₄—CF₃ | b | 80 |

-continued

| | | | | |
|---|---|---|---|---|
| 252 | naphthyl-CH(-)-CH(CH₃)₂ | N(COCF₃)(2-F-C₆H₃-CH(CH₃)-)(3-F-C₆H₄) | c | 86 |
| 253 | 3,4-(OCH₂O)-C₆H₃-C(CH₃)(CCl₂-) | N(COCH₃)(C₆H₅)(-CH(CN)C₆H₄-) | a | 87 |
| 254 | CF₃-C(Cl)=CH-cyclopropyl(CH₃)₂ | -CH(CN)-C₆H₄-CF(H)-C₆H₄-OCH₃ | g | 89 |
| 255 | 3-Cl-C₆H₄-CH(-)-CH(CH₃)₂ | -CH(CN)-C₆H₄-CF₂-C₆H₄-Br | c | 90 |
| 256 | 3,4-Cl₂-C₆H₃-C(CN)=CH-cyclopropyl(CH₃)₂ | -CH(C≡CH)-C₆H₄-C(OCH₃)(F)-C₆H₅ | d | 77 |
| 257 | 4-CH₃-C₆H₄-NH-CH(-)-CH(CH₃)₂ | -CH(CH₃)-(3-CF₃-5-)-C₆H₃-C(CH₂Br)(H)-C₆H₄-CH₂CH₃ | b | 82 |
| 258 | spiro cyclopropane-cyclopropane(CH₃)₂ | -CH(CH₃)-(3-Br-)-C₆H₃-C(CH₂CH₃)(H)-C₆H₄-Cl | e | 79 |
| 259 | Cl₂C=CH-O-cyclopropyl(CH₃)₂ | -CH(CN)-C₆H₄-C(Cl)(F)-C₆H₄-CF₃ | a | 85 |
| 260 | 4-Cl-C₆H₄-C(cyclopropyl)(-) | -CH(CN)-C₆H₄-C(F)(H)-C₆H₅ | b | 83 |
| 261 | CH≡C-CH₂-O-cyclopropyl(CH₃)₂ | -CH₂-C₆H₄-C(CF₃)(H)-C₆H₄-OCH₃ | a | 86 |

| 262 | 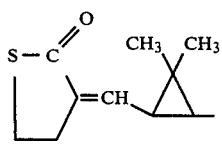 | 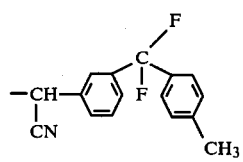 | g | 80 |

|  | Compound |  | Elementary analysis |  |  |  |
|---|---|---|---|---|---|---|
|  |  |  | C | H | N |  |
|  | 242 | Found | 69.85 | 6.76 | 3.31 | $C_{24}H_{28}NO_3Cl$ |
|  |  | Calculated | 69.63 | 6.83 | 3.38 |  |
|  | 243 | Found | 66.08 | 4.93 | 6.27 | $C_{25}H_{22}N_2O_2Cl_2$ |
|  |  | Calculated | 66.22 | 4.90 | 6.18 |  |
|  | 244 | Found | 68.56 | 6.31 | 6.24 | $C_{26}H_{28}N_2O_3F_2$ |
|  |  | Calculated | 68.70 | 6.22 | 6.16 |  |
|  | 245 | Found | 45.06 | 3.69 | 2.40 | $C_{22}H_{22}NO_3Br_3$ |
|  |  | Calculated | 44.92 | 3.78 | 2.38 |  |
|  | 246 | Found | 64.15 | 4.75 | 8.79 | $C_{26}H_{23}N_3O_2F_4$ |
|  |  | Calculated | 64.31 | 4.78 | 8.66 |  |
|  | 247 | Found | 72.69 | 5.04 | 3.08 | $C_{27}H_{23}NO_3F_2$ |
|  |  | Calculated | 72.46 | 5.19 | 3.13 |  |
|  | 248 | Found | 60.37 | 5.02 | 3.01 | $C_{23}H_{23}NO_2F_6$ |
|  |  | Calculated | 60.12 | 5.06 | 3.05 |  |
|  | 249 | Found | 67.40 | 4.89 | 2.95 | $C_{27}H_{23}NO_3Cl_2$ |
|  |  | Calculated | 67.50 | 4.84 | 2.92 |  |
|  | 250 | Found | 80.52 | 8.20 | 3.39 | $C_{27}H_{33}NO_2$ |
|  |  | Calculated | 80.34 | 8.26 | 3.47 |  |
|  | 251 | Found | 67.18 | 4.76 | 2.65 | $C_{28}H_{24}NO_2F_5$ |
|  |  | Calculated | 67.05 | 4.83 | 2.79 |  |
|  | 252 | Found | 67.22 | 4.59 | 2.50 | $C_{31}H_{26}NO_3F_5$ |
|  |  | Calculated | 67.01 | 4.73 | 2.52 |  |
|  | 253 | Found | 61.74 | 3.93 | 5.42 | $C_{27}H_{20}N_2O_5Cl_2$ |
|  |  | Calculated | 61.96 | 3.86 | 5.35 |  |
|  | 254 | Found | 60.77 | 4.45 | 2.79 | $C_{25}H_{22}NO_3F_4Cl$ |
|  |  | Calculated | 60.54 | 4.48 | 2.82 |  |
|  | 255 | Found | 58.41 | 4.02 | 2.71 | $C_{26}H_{21}NO_2F_2ClBr$ |
|  |  | Calculated | 58.60 | 3.98 | 2.63 |  |
|  | 256 | Found | 68.75 | 4.11 | 2.46 | $C_{32}H_{23}NO_3FCl_2$ |
|  |  | Calculated | 68.69 | 4.15 | 2.50 |  |
|  | 257 | Found | 63.28 | 5.80 | 2.34 | $C_{31}H_{34}NO_2F_3Br$ |
|  |  | Calculated | 63.15 | 5.82 | 2.38 |  |
|  | 258 | Found | 63.17 | 5.90 | — | $C_{25}H_{28}O_2ClBr$ |
|  |  | Calculated | 63.09 | 5.94 | — |  |
|  | 259 | Found | 52.54 | 3.16 | 2.39 | $C_{24}H_{18}NO_3F_4Cl_3$ |
|  |  | Calculated | 52.33 | 3.30 | 2.54 |  |
|  | 260 | Found | 71.85 | 4.92 | 3.26 | $C_{26}H_{21}NO_2FCl$ |
|  |  | Calculated | 71.96 | 4.89 | 3.23 |  |
|  | 261 | Found | 67.40 | 5.68 | — | $C_{25}H_{25}O_4F_3$ |
|  |  | Calculated | 67.25 | 5.66 | — |  |
|  | 262 | Found | 67.49 | 5.13 | 2.87 | $C_{27}H_{25}NO_3SF_2$ |
|  |  | Calculated | 67.33 | 5.24 | 2.91 |  |

The compounds of this invention are novel compounds which are solid or liquid at ordinary room temperature, and which are easily soluble in organic solvents in general. If they are employed for preparing an insecticide for use by spraying, therefore, they may take the form of an emulsifiable concentrate, an oily preparation, a powder preparation, a wettable powder, an aerosol, or the like. They can also be used for preparing an insecticide for use by fumigation, such as a mosquito-repellent incense, if they are mixed with an appropriate substrate, such as wood dust. The compounds may also be useful in preparing a so-called electric mosquito repellent in the form of a solution in an appropriate solvent, or a paper base impregnated with a solution thereof in an appropriate organic solvent. The electric mosquito repellent may be heated by an appropriate heater, and vaporized. Moreover, they exhibit equally outstanding effects in repelling mosquitoes when vaporized by a chemical heater, or by employing a sublimable assistant such as adamantane, cyclododecane or trimethylenenorbornane. The chemical heater which generates heat when contacted with air or water may, for example, comprise a composition of sodium sulfide and carbon, a composition of salt, iron and carbon, a composition of salt, iron, carbon and sodium metasilicate, or unslaked lime.

The compounds of this invention are stable against light as compared with the known chrysanthemumic ester pyrethroid, have a wide insecticidal spectrum, can effectively kill insects which are resistant to known organic phosphorus or carbamate insecticides, have low degrees of toxicity, and are inexpensive. For these reasons, the compounds of this invention are very useful substitutes for the known organic phosphorus or chlorine insecticides for agricultural and gardening uses. The compounds of this invention are very useful for the extermination of hygienically harmful insects such as flies, mosquitoes, and cockroaches; agriculturally harmful insects, which are resistant to organic phosphorus or carbamate insecticides, such as green rice leaf hoppers, plant-hoppers, rice stem borers, bean bugs, cabbage armyworms, diamond-back moths, oriental tobacco budworms, seed beetles, owlet moths and underwings, common cabbage worms, Japanese giant silk moths, leaf rollers, aphids, mealy bugs and scale insects, and rice weevils; and other insects which are harmful to cereals in stock, mites, and the like. It is possible to enhance further the insecticidal action of the compounds according to this invention, through use with a synergist such as N-octylbicycloheptenedicarboxyimide known under the trade name of MGK-264, a mixture thereof with an arylsulfonate known under the trade name of MGK-5026, N-octyl-1-isopropyl-4-methylbicyclo [2,2,2]octo-5-ene-2,3-dicarboxyimide, octachlorodipropylether, or piperonylbutoxide. It is also possible to increase the stability of the compounds according to this invention to a further extent by adding BHT, DBHQ, or the like as stabilizer or oxidation inhibitor thereto, if required. It is further possible to mix with the compound of this invention other insecticides, including an organic phosphorus insecticide such as fenitrotion, DDVP, diazinon, propaphos, or pyridaphenthion, a carbamate such as NAC, MTMC, BPMC or PHC, a pyrethroid such as pyrethrin, allethrin, phthalthrin, furamethrin, phenothrin, permethrin, cypermethrin, decamethrin, fenevalerate or fenpropanate, other insecticides such as cartap, chlorophenamidine or methomyl, an acaricide, a germicide, a nematocide, a herbicide, a plant growth regulator, a fertilizer, or other agrochemicals. The mixture provides a multi-purpose composition which is outstandingly effective against harmful insects of the kind which resist an organic phosphorus or carbamate insecticide. The use of any such mixture contributes to saving the labor which is required for application of the individual chemicals, while it produces the synergistic effects of the individual chemicals.

The following is a description of results of the tests conducted for ascertaining the superior effects of the compounds and the composition containing them according to this invention.

TEST EXAMPLE 1

Insecticidal Tests by Spraying

There were prepared a 0.2% kerosene solution of each of the compounds according to this invention, or allethrin or phthalthrin (control) (Group A), a kerosene solution containing 0.2% of each of the compounds according to this invention, and 0.8% of piperonyl butoxide (Group B), and a kerosene solution containing 0.1% of each compound according to this invention, and 0.1% of phthalthrin (Group C). With respect to each of the solutions thus prepared, their knockdown rate of houseflies was determined. Relative effectiveness of the test compounds was calculated taking the knockdown rate of allethrin as 1.00. following table shows the mortality after 24 hours. In the table, the figures indicate the knockdown rates and those in the parentheses indicate the mortality after 24 hours.

| Test compound | (A) | (B) | (C) |
|---|---|---|---|
| Allethrin | 1.00(26) | — | — |
| Phthalthrin | 2.15(34) | — | — |
| (1) | 3.49(100) | 5.70(100) | 2.94(100) |
| (2) | 4.07(100) | 6.34(100) | 3.31(100) |
| (3) | 2.95(100) | 4.58(100) | 2.60(100) |
| (4) | 3.18(100) | 5.43(100) | 2.85(100) |
| (5) | 3.32(100) | 5.29(100) | 2.77(100) |
| (6) | 3.41(100) | 5.62(100) | 2.96(100) |
| (7) | 3.50(100) | 5.45(100) | 2.98(100) |
| (8) | 2.93(100) | 4.90(100) | 2.61(100) |
| (9) | 3.34(100) | 5.63(100) | 2.92(100) |
| (10) | 3.16(100) | 5.49(100) | 2.73(100) |
| (11) | 2.35(89) | 4.18(100) | 2.30(100) |

-continued

| Test compound | (A) | (B) | (C) |
|---|---|---|---|
| (12) | 2.82(100) | 4.95(100) | 2.65(100) |
| (13) | 3.27(100) | 5.60(100) | 2.98(100) |
| (14) | 2.21(85) | 4.06(100) | 2.29(100) |
| (15) | 2.46(100) | 4.30(100) | 2.31(100) |
| (16) | 2.65(100) | 4.72(100) | 2.44(100) |
| (17) | 2.53(100) | 4.68(100) | 2.37(100) |
| (18) | 2.59(100) | 4.70(100) | 2.45(100) |
| (19) | 2.83(100) | 4.93(100) | 2.51(100) |
| (20) | 2.44(100) | 4.55(100) | 2.36(100) |
| (21) | 2.97(100) | 5.06(100) | 2.59(100) |
| (22) | 2.98(100) | 4.82(100) | 2.63(100) |
| (23) | 2.85(100) | 4.79(100) | 2.58(100) |
| (24) | 3.02(100) | 5.14(100) | 2.68(100) |
| (25) | 2.59(100) | 4.80(100) | 2.46(100) |
| (26) | 2.98(100) | 5.05(100) | 2.61(100) |
| (27) | 2.46(100) | 4.39(100) | 2.37(100) |
| (28) | 2.75(100) | 4.91(100) | 2.53(100) |
| (29) | 2.50(100) | 4.72(100) | 2.34(100) |
| (30) | 2.41(100) | 4.56(100) | 2.35(100) |
| (31) | 2.32(92) | 4.17(100) | 2.35(100) |
| (32) | 2.24(85) | 4.23(100) | 2.29(100) |
| (33) | 2.58(100) | 4.82(100) | 2.40(100) |
| (34) | 2.65(100) | 4.88(100) | 2.51(100) |
| (35) | 2.47(100) | 4.54(100) | 2.38(100) |
| (36) | 2.73(100) | 4.85(100) | 2.57(100) |
| (37) | 2.40(100) | 4.49(100) | 2.35(100) |
| (38) | 2.21(82) | 3.97(100) | 2.29(97) |
| (39) | 2.40(100) | 4.36(100) | 2.41(100) |
| (40) | 2.47(100) | 4.50(100) | 2.45(100) |
| (41) | 2.39(100) | 4.28(100) | 2.42(100) |
| (42) | 2.37(100) | 4.30(100) | 2.39(100) |
| (43) | 2.24(92) | 4.19(100) | 2.27(100) |
| (44) | 2.43(100) | 4.41(100) | 2.40(100) |
| (45) | 2.36(100) | 4.06(100) | 2.38(100) |
| (46) | 2.48(100) | 4.71(100) | 2.43(100) |
| (47) | 3.19(100) | 5.27(100) | 2.67(100) |
| (48) | 2.91(100) | 4.94(100) | 2.56(100) |
| (49) | 3.21(100) | 5.05(100) | 2.74(100) |
| (50) | 3.43(100) | 5.26(100) | 2.81(100) |
| (51) | 4.04(100) | 6.23(100) | 3.05(100) |
| (52) | 1.96(86) | 3.06(100) | 2.07(100) |
| (53) | 2.58(100) | 4.71(100) | 2.42(100) |
| (54) | 2.07(85) | 3.39(100) | 2.18(100) |
| (55) | 2.63(100) | 4.73(100) | 2.49(100) |
| (56) | 2.59(100) | 4.38(100) | 2.40(100) |
| (57) | 1.92(84) | 3.27(100) | 2.05(98) |
| (58) | 2.77(100) | 4.42(100) | 2.56(100) |
| (59) | 2.78(100) | 4.38(100) | 2.47(100) |
| (60) | 2.56(100) | 4.24(100) | 2.41(100) |
| (61) | 2.62(100) | 4.55(100) | 2.49(100) |
| (62) | 2.54(100) | 4.37(100) | 2.40(100) |
| (63) | 3.16(100) | 5.08(100) | 2.65(100) |
| (64) | 2.73(100) | 4.67(100) | 2.49(100) |
| (65) | 1.81(82) | 3.06(100) | 2.07(90) |
| (66) | 2.44(100) | 4.25(100) | 2.36(100) |
| (67) | 2.15(90) | 4.07(100) | 2.20(100) |
| (68) | 1.76(70) | 2.99(97) | 2.04(85) |
| (69) | 2.28(97) | 3.85(100) | 2.27(100) |
| (70) | 1.91(80) | 3.34(100) | 2.12(88) |
| (71) | 2.23(90) | 3.68(100) | 2.26(100) |
| (72) | 2.57(100) | 4.61(100) | 2.43(100) |
| (73) | 1.87(77) | 2.85(100) | 2.08(82) |
| (74) | 2.60(100) | 4.59(100) | 2.51(100) |
| (75) | 3.24(100) | 5.10(100) | 2.86(100) |
| (76) | 3.31(100) | 5.24(100) | 2.92(100) |
| (77) | 3.87(100) | 6.09(100) | 3.15(100) |
| (78) | 3.40(100) | 5.76(100) | 2.93(100) |
| (79) | 3.03(100) | 5.18(100) | 2.77(100) |
| (80) | 2.92(100) | 4.91(100) | 2.64(100) |
| (81) | 3.16(100) | 5.07(100) | 2.71(100) |
| (82) | 2.88(100) | 4.75(100) | 2.68(100) |
| (83) | 2.51(100) | 4.32(100) | 2.49(100) |
| (84) | 2.76(100) | 4.69(100) | 2.50(100) |
| (85) | 2.63(100) | 4.54(100) | 2.42(100) |
| (86) | 2.59(100) | 4.42(100) | 2.34(100) |
| (87) | 2.47(100) | 4.25(100) | 2.40(100) |
| (88) | 2.11(87) | 3.84(100) | 2.23(100) |
| (89) | 3.07(100) | 4.91(100) | 2.65(100) |
| (90) | 2.86(100) | 4.73(100) | 2.56(100) |
| (91) | 2.56(100) | 4.70(100) | 2.43(100) |
| (92) | 2.91(100) | 4.98(100) | 2.68(100) |

| Test compound | (A) | (B) | (C) |
| --- | --- | --- | --- |
| (93) | 2.85(100) | 4.80(100) | 2.53(100) |
| (94) | 2.42(100) | 4.25(100) | 2.39(100) |
| (95) | 2.53(100) | 4.39(100) | 2.41(100) |
| (96) | 2.38(100) | 4.14(100) | 2.32(100) |
| (97) | 2.50(100) | 4.47(100) | 2.41(100) |
| (98) | 2.09(84) | 3.63(100) | 2.27(97) |
| (99) | 2.54(100) | 4.71(100) | 2.40(100) |
| (100) | 2.61(100) | 4.79(100) | 2.48(100) |
| (101) | 2.38(100) | 4.22(100) | 2.33(100) |
| (102) | 2.94(100) | 4.95(100) | 2.65(100) |
| (103) | 2.40(100) | 4.23(100) | 2.36(100) |
| (104) | 2.51(100) | 4.64(100) | 2.40(100) |
| (105) | 2.59(100) | 4.70(100) | 2.44(100) |
| (106) | 2.86(100) | 4.85(100) | 2.61(100) |
| (107) | 3.15(100) | 5.26(100) | 2.79(100) |
| (108) | 2.82(100) | 4.89(100) | 2.58(100) |
| (109) | 1.98(80) | 3.26(100) | 2.16(90) |
| (110) | 2.07(90) | 3.74(100) | 2.19(100) |
| (111) | 2.60(100) | 4.57(100) | 2.42(100) |
| (112) | 1.71(75) | 2.84(95) | 2.08(80) |
| (113) | 1.60(72) | 2.57(90) | 2.04(76) |
| (114) | 2.53(100) | 4.60(100) | 2.41(100) |
| (115) | 1.96(80) | 3.25(100) | 2.12(87) |
| (116) | 2.53(100) | 4.49(100) | 2.39(100) |
| (117) | 1.88(78) | 2.91(97) | 2.16(85) |
| (118) | 2.33(100) | 4.28(100) | 2.30(100) |
| (119) | 2.79(100) | 4.68(100) | 2.54(100) |
| (120) | 2.51(100) | 4.59(100) | 2.37(100) |
| (121) | 2.05(82) | 3.43(97) | 2.19(90) |
| (122) | 2.60(100) | 4.58(100) | 2.46(100) |
| (123) | 1.93(80) | 3.40(100) | 2.12(87) |
| (124) | 2.18(92) | 3.86(100) | 2.23(100) |
| (125) | 1.80(72) | 2.92(92) | 1.98(82) |
| (126) | 2.51(100) | 4.30(100) | 2.44(100) |
| (127) | 1.96(82) | 3.03(100) | 2.07(100) |
| (128) | 1.87(75) | 2.86(92) | 1.98(82) |
| (129) | 2.43(100) | 4.39(100) | 2.35(100) |
| (130) | 2.56(100) | 4.48(100) | 2.40(100) |
| (131) | 2.59(100) | 4.64(100) | 2.43(100) |
| (132) | 2.38(100) | 4.31(100) | 2.30(100) |
| (133) | 2.40(100) | 4.26(100) | 2.32(100) |
| (134) | 1.70(68) | 2.75(88) | 1.96(75) |
| (135) | 2.39(100) | 4.17(100) | 2.40(100) |
| (136) | 2.64(100) | 4.71(100) | 2.48(100) |
| (137) | 2.45(100) | 4.32(100) | 2.42(100) |
| (138) | 2.41(100) | 4.39(100) | 2.37(100) |
| (139) | 2.42(100) | 4.30(100) | 2.36(100) |
| (140) | 1.98(85) | 3.07(97) | 2.15(100) |
| (141) | 2.17(97) | 3.96(100) | 2.24(100) |
| (142) | 2.49(100) | 4.41(100) | 2.42(100) |
| (143) | 2.36(100) | 4.25(100) | 2.29(100) |
| (144) | 2.48(100) | 4.38(100) | 2.41(100) |
| (145) | 2.16(92) | 3.70(100) | 2.19(100) |
| (146) | 2.37(100) | 4.23(100) | 2.36(100) |
| (147) | 2.03(92) | 3.89(100) | 2.20(100) |
| (148) | 2.34(100) | 4.16(100) | 2.31(100) |
| (149) | 2.42(100) | 4.08(100) | 2.35(100) |
| (150) | 1.98(85) | 3.25(100) | 2.13(97) |
| (151) | 2.41(100) | 3.99(100) | 2.33(100) |
| (152) | 2.49(100) | 4.34(100) | 2.41(100) |
| (153) | 3.19(100) | 4.98(100) | 2.84(100) |
| (154) | 3.21(100) | 5.04(100) | 2.90(100) |
| (155) | 3.05(100) | 4.86(100) | 2.72(100) |
| (156) | 3.34(100) | 5.37(100) | 2.91(100) |
| (157) | 3.36(100) | 5.40(100) | 2.93(100) |
| (158) | 3.08(100) | 5.11(100) | 2.69(100) |
| (159) | 2.96(100) | 4.85(100) | 2.64(100) |
| (160) | 2.74(100) | 4.72(100) | 2.50(100) |
| (161) | 3.13(100) | 5.23(100) | 2.77(100) |
| (162) | 2.70(100) | 4.85(100) | 2.54(100) |
| (163) | 2.69(100) | 4.76(100) | 2.48(100) |
| (164) | 2.72(100) | 4.81(100) | 2.55(100) |
| (165) | 2.41(100) | 4.29(100) | 2.38(100) |
| (166) | 2.28(94) | 3.97(100) | 2.25(100) |
| (167) | 2.06(90) | 3.70(100) | 2.23(100) |
| (168) | 2.63(100) | 4.39(100) | 2.49(100) |
| (169) | 2.04(87) | 3.80(100) | 2.17(100) |
| (170) | 1.86(80) | 3.21(100) | 2.04(90) |
| (171) | 2.13(90) | 3.82(100) | 2.19(100) |
| (172) | 1.73(75) | 2.83(92) | 2.02(82) |
| (173) | 2.30(100) | 4.16(100) | 2.31(100) |
| (174) | 2.78(100) | 4.87(100) | 2.57(100) |
| (175) | 1.96(84) | 3.17(100) | 2.08(92) |
| (176) | 2.91(100) | 4.88(100) | 2.62(100) |
| (177) | 2.82(100) | 4.79(100) | 2.57(100) |
| (178) | 2.85(100) | 4.83(100) | 2.56(100) |
| (179) | 2.76(100) | 4.80(100) | 2.54(100) |
| (180) | 2.54(100) | 4.69(100) | 2.39(100) |
| (181) | 2.58(100) | 4.75(100) | 2.38(100) |
| (182) | 2.03(83) | 3.27(100) | 2.17(92) |
| (183) | 2.19(92) | 3.62(100) | 2.23(100) |
| (184) | 1.82(80) | 3.04(100) | 2.05(90) |
| (185) | 2.55(100) | 4.82(100) | 2.41(100) |
| (186) | 1.73(77) | 2.95(95) | 2.05(85) |
| (187) | 2.26(95) | 3.67(100) | 2.23(100) |
| (188) | 2.73(100) | 4.68(100) | 2.56(100) |
| (189) | 2.79(100) | 4.73(100) | 2.54(100) |
| (190) | 2.40(100) | 4.26(100) | 2.31(100) |
| (191) | 2.30(100) | 4.12(100) | 2.27(100) |
| (192) | 1.94(87) | 3.22(100) | 2.12(100) |
| (193) | 2.41(100) | 4.29(100) | 2.33(100) |
| (194) | 2.50(100) | 4.41(100) | 2.34(100) |
| (195) | 1.86(82) | 3.17(97) | 2.07(92) |
| (196) | 2.28(97) | 4.15(100) | 2.20(100) |
| (197) | 2.51(100) | 4.84(100) | 2.38(100) |
| (198) | 2.49(100) | 4.80(100) | 2.37(100) |
| (199) | 2.48(100) | 4.79(100) | 2.34(100) |
| (200) | 2.60(100) | 4.81(100) | 2.48(100) |
| (201) | 2.63(100) | 4.92(100) | 2.42(100) |
| (202) | 2.57(100) | 4.85(100) | 2.33(100) |
| (203) | 2.14(85) | 3.56(100) | 2.23(100) |
| (204) | 1.81(75) | 2.87(97) | 2.06(84) |
| (205) | 2.50(100) | 4.72(100) | 2.37(100) |
| (206) | 2.39(100) | 4.48(100) | 2.30(100) |
| (207) | 2.87(100) | 5.01(100) | 2.56(100) |
| (208) | 2.64(100) | 4.73(100) | 2.41(100) |
| (209) | 2.50(100) | 4.69(100) | 2.32(100) |
| (210) | 2.52(100) | 4.72(100) | 2.40(100) |
| (211) | 2.26(100) | 4.31(100) | 2.24(100) |
| (212) | 2.44(100) | 4.38(100) | 2.31(100) |
| (213) | 2.16(84) | 3.64(100) | 2.25(100) |
| (214) | 2.03(80) | 3.17(100) | 2.19(100) |
| (215) | 1.77(72) | 2.90(95) | 1.93(80) |
| (216) | 2.55(100) | 4.66(100) | 2.41(100) |
| (217) | 2.58(100) | 4.70(100) | 2.43(100) |
| (218) | 1.71(70) | 2.83(95) | 1.99(85) |
| (219) | 1.98(84) | 3.12(97) | 2.16(92) |
| (220) | 2.49(100) | 4.86(100) | 2.33(100) |
| (221) | 2.52(100) | 4.92(100) | 2.37(100) |
| (222) | 2.36(100) | 4.78(100) | 2.31(100) |
| (223) | 1.98(84) | 3.13(100) | 2.09(97) |
| (224) | 2.25(100) | 4.24(100) | 2.26(100) |
| (225) | 2.01(85) | 3.29(100) | 2.14(100) |
| (226) | 2.26(97) | 4.11(100) | 2.25(100) |
| (227) | 1.73(70) | 2.86(92) | 1.98(82) |
| (228) | 2.45(100) | 4.71(100) | 2.30(100) |
| (229) | 1.98(85) | 3.17(100) | 2.16(100) |
| (230) | 2.40(100) | 4.58(100) | 2.32(100) |
| (231) | 2.19(92) | 4.02(100) | 2.17(100) |
| (232) | 3.03(100) | 4.64(100) | 2.61(100) |
| (233) | 2.72(100) | 4.88(100) | 2.50(100) |
| (234) | 1.86(84) | 3.16(100) | 2.04(100) |
| (235) | 2.62(100) | 4.78(100) | 2.45(100) |
| (236) | 2.24(100) | 4.30(100) | 2.21(100) |
| (237) | 2.63(100) | 4.80(100) | 2.42(100) |
| (238) | 2.51(100) | 4.97(100) | 2.49(100) |
| (239) | 2.38(100) | 4.50(100) | 2.35(100) |
| (240) | 2.43(100) | 5.02(100) | 2.34(100) |
| (241) | 2.30(100) | 4.76(100) | 2.33(100) |

As seen from the above table, the insecticides containing the compounds according to the present invention have extremely high knock-down effects, and their killing effects are far higher compared with the conventional pyrethroid such as allethrin, phthalthrin.

TEST EXAMPLE 2

Insecticidal Tests by Spraying

There were prepared a 0.02% kerosene solution of each of the optical isomers of the compounds according to this invention, or allethrin or phthalthrin (control) (Group A), a kerosene solution containing 0.02% of each of the compounds according to this invention, and 0.1% of piperonyl butoxide (Group B), and a kerosene solution containing 0.01% of each compound according to this invention, and 0.01% of phthalthrin (Group C).

Each of the solutions thus prepared was sprayed by means of a turn table. The relative effective rates of the knockdown effects of the tested compounds was calculated from the knockdown rates of the house flies 1, 2, 5, 10 and 20 minutes after spraying, and the mortalities of the house flies after 24 hours were determined. The control compounds are shown in the following table by giving the numbers A, B and C after their compound Nos. The alcohol components in these compounds are the same as those of the original ones. The parentheses mean the mortality after 24 hours.

| Compounds | (A) | (B) | (C) |
|---|---|---|---|
| Allethrin | 1.00(5) | — | — |
| Phthalthrin | 2.15(8) | — | — |
| (1)* (S)3'-anilino-α'-cyano-benzyl (1R,3S)2,2-dimethyl-3-(2,2-dichlorovinyl)-cyclopropane carboxylate | 24.6(100) | 37.2(100) | 13.7(100) |
| (1)* - A [acid has (1R,3R) form] | 5.0(100) | 10.4(100) | 3.1(100) |
| (1)* - B [acid has (1RS)-cis form] | 12.1(100) | 19.8(100) | 7.6(100) |
| (2)* (RS)3'-anilino-α'-cyano-benzyl (1R,3S)2,2-dimethyl-3-(2,2-dibromovinyl)cyclopropane carboxylate | 20.8(100) | 34.5(100) | 11.9(100) |
| (2)* - A [acid has (1R,3R) form] | 4.3(100) | 9.1(100) | 3.4(100) |
| (2)* - C [acid has (1RS)-cis/trans form] | 4.6(100) | 10.4(100) | 3.5(100) |

As seen from the above table, among halovinyl chrysanthemumic acid esters, the insecticidal effects of the (1R,3S), or d-cis forms have the highest insecticidal effects, and their knockdown effects are higher 3–5 times that of the corresponding d-trans forms.

TEST EXAMPLE 3

Insecticidal test by topical application method

A predetermined-concentration acetone solution of each of phenothrin, the compounds according to the present invention (Group A), and an acetone solution containing said predetermined concentration of each of phenothrine, the compounds according to the present invention, and said by two times of predetermined concentration of cynepirin 500 were prepared. Each solution was applied to the back of the house fly by means of microsyringe. From the mortality after 24 hours, the relative mortality with respect to phenothrin, and the synergistic effect of the cyneprin 500 were determined.

Note is to be taken that the compounds having the mark * were examined using 3'-benzylbenzyl 2,2-dimethyl-3-(2,2-dimethylvinyl)cyclopropane carboxylate as control.

As shown in the following table, each of the examined compounds according to the present invention has far superior insecticidal effect to that of the controls.

| Test compound | Relative insecticidal activity | Relative insecticidal activity when synergist added | Increase by (times) |
|---|---|---|---|
| Phenothrin | 1.00 | 1.85 | 1.9 |
| (2) | 6.25 | 16.88 | 2.7 |
| (4) | 2.38 | 6.90 | 2.9 |
| (10) | 3.86 | 11.58 | 3.0 |
| (26) | 3.54 | 9.91 | 2.8 |
| (33) | 3.25 | 10.08 | 3.1 |
| (63) | 3.48 | 9.05 | 2.6 |
| (75) | 3.57 | 8.93 | 2.5 |
| (82) | 3.25 | 8.45 | 2.6 |
| (95) | 3.76 | 9.02 | 2.4 |
| (104) | 3.04 | 8.21 | 2.7 |
| (116) | 3.65 | 8.76 | 2.4 |
| (130) | 3.28 | 9.51 | 2.9 |
| (142) | 3.02 | 7.85 | 2.6 |
| 3'-benzylbenzyl 2,2-dimethyl-3-(2,2-dimethylvinyl) cyclopropane carboxylate chrysanthemate | 1.00 | 1.72 | 1.7 |
| (166)* | 3.15 | 10.08 | 3.2 |
| (181)* | 3.40 | 9.86 | 2.9 |
| (200)* | 3.39 | 10.17 | 3.0 |
| (221)* | 4.03 | 11.28 | 2.8 |

In the following, the formulation of the compounds according to the present invention will be described, but it is understood that there is not needed any special condition therefor and it can be done by the methods with which the skilled in the art to which the present invention pertains are well familiar.

Formulation 1

Kerosene is added to 0.2 parts of each of the compounds (2), (34), (76), (89), (154), and (191) to form 0.2% of oily preparation.

Formulation 2

Kerosene is added to 0.2 parts of each of compounds (6), (43), (81), (118), (159) and (203), and 0.8 parts of pyperonylbutoxide to form of 100 parts of oily preparation.

Formulation 3

20% emulsifiable concentrate are prepared by kneading 20 parts of each of compounds (10), (23), (84), (120), (162) and (214), 10 parts of solpol SM-200 (Trademark of Toho Chemical Industries, Ltd.), and 70 parts of xylol.

Formulation 4

0.4 parts of each of the compounds (15), (41), (100), (135), (176) and (227) of this invention, 0.1 part of resmethrin and 1.5 parts of octachlorodipropylether were dissolved in 28 parts of refined kerosene. The solution was packed into an aerosol container and after a valve arrangement had been attached to the container, 70 parts of a jetting agent (liquefied petroleum gas) were filled under pressure into the container through its valve arrangement to prepare an aerosol.

Formulation 5

0.5 g of each of the compounds (14), (33), (78), (111), (187) and (230) of this invention and 0.5 g of BHT were mixed uniformly with 99.0 g of a substrate for a mosquito-repellent incense, such as pyrethrum, wood, flour starch and the like. The mixture was formed into a mosquito-repellent incense by a known method.

Formulation 6

0.4 g of each of the compounds (25), (46), (90), (124), (171) and (206) of this invention and 1.0 g of MGK-5026 were mixed uniformly with 98.6 g of a substrate for a mosquito-repellent incense. The mixture was formed into a mosquito-repellent incense by a known method.

Formulation 7

Three parts of each of the compounds (8), (55), (82), (141), (169) and (224) of this invention and 99.7 parts of clay were crushed well and mixed together to yield a 0.3% powder.

Formulation 8

A wettable powder was obtained by crushing and mixing 40 parts of each of the compounds (37), (64), (96), (150), (192) and (235) of this invention, 35 parts of diatomaceous earth, 20 parts of clay, 3 parts of a laurylsulfonate and 2 parts of carboxymethyl cellulose.

TEST EXAMPLE 4

Each emulsifiable concentrate containing compounds (2), (5), (10), (23), (36), (58), (72), (84), (98), (106), (120), (139), (157), (162), (180), (195), (207), (214) and (238) of the present invention, which are prepared by the method mentioned in formulation 3, was diluted with water to prepare 1/1000 solution. 100 l/10a of the solution was sprayed onto Japanese radish leaves at the 5-6 leaf stage, on which a lot of green peach aphid (*Myzus persicae* Sulzer) were grown all over the surface. After 2 days, the green peach aphids decreased to less than 1/10 in each case when compared to those before spraying.

TEST EXAMPLE 5

Cabbage leaves were immersed for about five seconds into 1/2000 diluted solutions of emulsifiable concentrates of containing the compounds (3), (8), (10), (23), (39), (63), (84), (102), (120), (137), (148), (162), (170), (196), (214) and (229). After the coating is dried, the leaves are put in a glass vessel in which 10 sound larvae of cabbage armyworm are settled. The larvae are supplied twice at the date when the test leaves are prepared and 5 days after that date. Mortality of Compounds tested after 24 hrs. is listed as follows:

| Test compound | 1st day after immersion | 5th day after immersion |
| --- | --- | --- |
| Salithion emulsion | 40 (%) | 5 (%) |
| (3) | 100 | 100 |
| (8) | 100 | 90 |
| (10) | 100 | 95 |
| (23) | 100 | 100 |
| (39) | 100 | 90 |
| (63) | 85 | 75 |
| (84) | 100 | 100 |
| (102) | 95 | 85 |
| (120) | 85 | 75 |
| (137) | 100 | 95 |
| (148) | 90 | 85 |
| (162) | 100 | 100 |
| (170) | 100 | 85 |
| (196) | 80 | 70 |
| (214) | 90 | 85 |
| (229) | 95 | 85 |

TEST EXAMPLE 6

About 200 aphids (*Aphis craccivora* Koch) were put free on each broad bean plant (*Vicia faba* L) in a pot one day prior to the application of an insecticide. 1/4000 diluted solutions of wettable powders containing the compounds (6), (11), (24), (37), (49), (64), (73), (96), (113), (131), (150), (166), (192), (208), (219), (220) and (241) respectively, of this invention prepared in accordance with the procedures of formulation 8 for Insecticide Preparation were sprayed by compressed air onto the leaves with the harmful insects at a rate of 10 ml per pot. After two days, the degree of damage was examined, and none of them was found to suffer from increased damage.

TEST EXAMPLE 7

Each powder containing (7), (12), (20), (35), (55), (61), (82), (103), (129), (141), (152), (169), (184), (202), (224) and (223) which was prepared by the formulation 7 was uniformly sprinkled at the ratio of 2 g/m² on the bottom of a tall glass vessel having a diameter of 14 cm and the butter is coated on the wall of the vessel leaving the portion 1 cm height from the bottom. A group consisting of 10 imagines *Blattella germanicas* were placed on the bottom of the vessel. After the group was put into contact with the powder for 30 minutes, it was transfered into a clean vessel. After two days, more than 80% of germanicas were killed with any of powders.

TEST EXAMPLE 8

Ten adult female carmine spider mites were put free on each of the four leaves of a kidney beanplant in a pot five days after seeding. The pot was kept in a room having a constant temperature of 27° C. After 6 days, 100 ppm water diluted solutions of emulsifiable concentrates of the compounds (10), (14), (23), (36), (51), (65), (84), (93), (117), (120), (136), (151), (162), (178), (193), (212) and (225), respectively, of this invention prepared in accordance with the procedures of formulation 3 for Insecticide Preparation were sprinkled to the pots on a twin table at the rate of 10 ml/pot. After 10 days, the plants were examined and only 10 or fewer ticks were found on each plant.

TEST EXAMPLE 9

TLm 48 (p.p.m.) values of the compounds (9), (18), (27), (38), (57), (74), (83), (105), (126), (147), (164), (181), (204), (218), (226) and (240) were determined more than 0.8 from the tests conducted in accordance with the toxicity test method as to fish which had been published in Agricultural policy B-2735 (Nov. 25, 1965) using carps.

What is claimed is:

1. A compound of the formula (I):

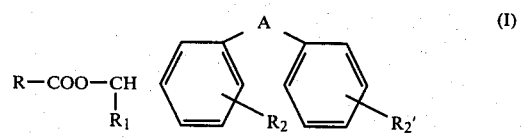

wherein R is the group (II), (III), (IV), (V), (VI), (VII), (VIII), (IX), (X), (XI), (XII) or (XIII):

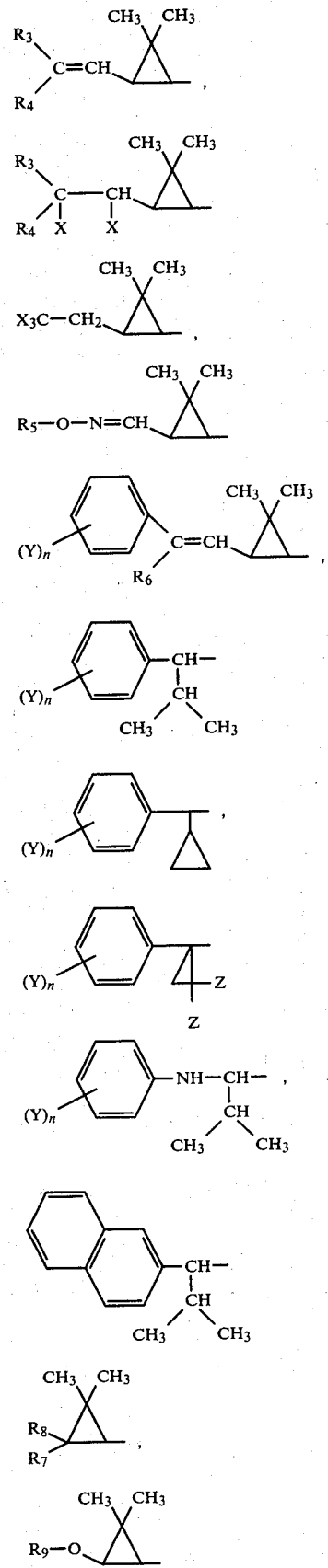

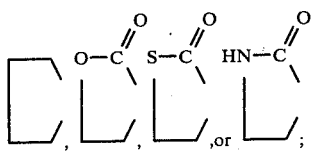

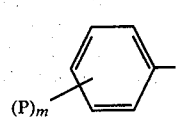

wherein $R_3$ and $R_4$, which are the same as or different from each other, are methyl group, halogen atom, or halomethyl group, or $R_3$ and $R_4$ together may form the ring:

X is halogen atom; $R_5$ is alkyl group having 1–3 carbon atoms; n is an integer of 1–3; $R_6$ is hydrogen atom, methyl group, halogen atom, or cyano group; Y is hydrogen atom, halogen atom, lower alkyl group, lower alkoxy group, lower alkylthio group, lower haloalkyl group, lower haloalkoxy group, lower haloalkylthio group, or methylenedioxy group; z is methyl group, fluorine atom, or chlorine atom; $R_7$ is methyl group or chlorine atom; $R_8$ is methyl group, chlorine atom, halomethyl group, methoxy group, or methoxymethyl group or $R_7$ and $R_8$ together may form ethylene- trimethylene- or tetramethylene-chain; $R_9$ is alkyl group having 1–6 carbon atoms, or cycloalkyl-, alkenyl-, haloalkyl-, haloalkenyl- or alkynyl-group, or the group of the formula (XIV):

$$\text{(XIV)}$$

wherein m is an integer of 1–2; P is hydrogen atom, halogen atom, lower alkyl group, lower alkoxy group, lower alkylthio group, lower haloalkyl group, lower haloalkoxy group, or methylenedioxy group; $R_1$ is hydrogen atom, cyano group, methyl group or ethynyl group; $R_2$, $R_2'$ are hydrogen atom, halogen atom, methyl group, trifluoromethyl group or lower alkoxy group; A is the group of the formula (XV) or (XVI):

$$\begin{array}{c} R_{10} \\ | \\ N \\ / \quad \backslash \end{array} \qquad \text{(XV)}$$

$$\begin{array}{c} R_{12} \\ | \\ C \\ / | \backslash \\ R_{11} \end{array} \qquad \text{(XVI)}$$

wherein $R_{10}$ is hydrogen atom, alkyl- or haloalkyl- group having 1–2 carbon atoms, halogen atom, formyl group, acetyl group or haloacetyl group, provided that in the group of the formula (XV) the nitrogen atom may form a salt of a strong inorganic acid or a strong organic acid; $R_{11}$ is hydrogen atom or fluorine atom; and $R_{12}$ is halogen atom, lower alkyl group, lower haloalkyl group or lower alkoxy group.

2. A compound according to claim 1, wherein A is the group of the formula (XV).

3. A compound according to claim 2, wherein R is the group of the formula (II), (III), (IV), (V), (VI), (XII), or (XIII).

4. A compound according to claim 2, wherein R is the group of the formula (VII), (X) or (XI).

5. A compound according to claim 2, wherein R is the group of the formula (VIII).

6. A compound according to claim 1, wherein A is the group o the formula (XVI).

7. A compound according to claim 6, wherein R is the group of the formula (II), (III), (IV), (V), (VI), (XII), or (XIII).

8. A compound according to claim 6, wherein R is the group of the formula (VII), (X) or (XI).

9. A compound according to claim 6, wherein R is the group of the formula (VIII) or (IX).

10. An insecticidal or acaricidal composition comprising as an essential ingredient an insecticidally or acaricidally effective amount of a compound of the formula (I):

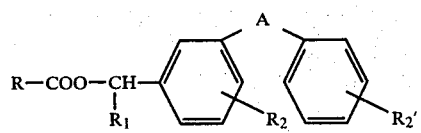  (I)

wherein R is the group (II), (III), (IV), (V), (VI), (VII), (VIII), (IX), (X), (XI), (XII) or (XIII):

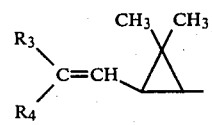  (II)

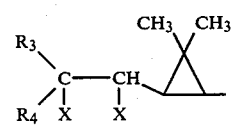  (III)

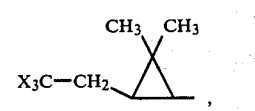  (IV)

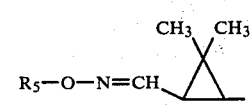  (V)

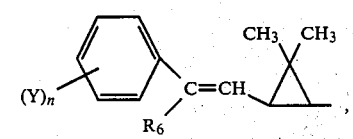  (VI)

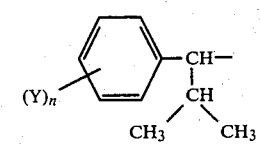  (VII)

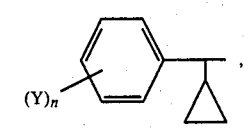  (VIII)

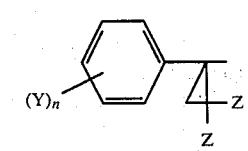  (IX)

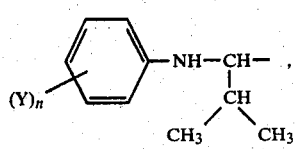  (X)

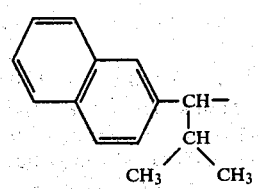  (XI)

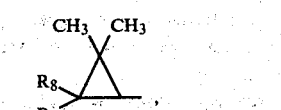  (XII)

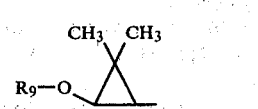  (XIII)

wherein $R_3$ and $R_4$, which are the same as or different from each other, are methyl group, halogen atom or halomethyl group, or $R_3$ and $R_4$ together may form the ring;

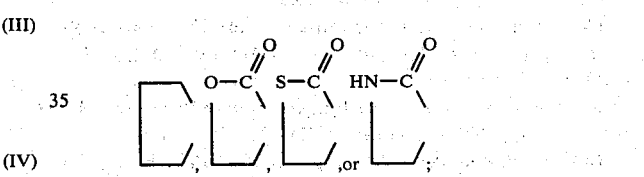

X is halogen atom; $R_5$ is alkyl group having 1–3 carbons; n is an integer of 1–3; $R_6$ is hydrogen atom, methyl group, halogen atom or cyano group; Y is hydrogen atom, halogen atom, lower alkyl group, lower alkoxy group, lower alkylthio group, lower haloalkyl group, lower haloalkoxy group, lower haloalkylthio group or methylenedioxy group; z is methyl group, fluorine atom or chlorine atom; $R_7$ is methyl group or chlorine atom; $R_8$ is methyl group, chlorine atom, halomethyl group, methoxy group or methoxymethyl group, or $R_7$ and $R_8$ together may form ethylene-, trimethylene-, tetramethylene-chain; $R_9$ is alkyl group or cycloalkyl-, alkenyl-, haloalkyl-, haloalkenyl- or alkynyl-group, or the group of the formula (XIV):

  (XIV)

wherein m is an integer of 1–2; P is hydrogen atom, halogen atom, lower alkyl group, lower alkoxy group, lower alkylthio group, lower haloalkyl group, lower haloalkoxy group or methylenedioxy group; $R_1$ is hydrogen atom, cyano group, methyl group or ethynyl group; $R_2$, $R_2'$ are hydrogen atom, halogen atom, methyl group, trifluoromethyl group or lower alkoxy group; A is the group of the formula (XV) or (XVI):

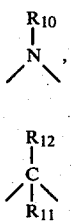

(XV)

(XVI)

wherein $R_{10}$ is hydrogen atom, alkyl- or haloalkyl-group having 1-2 carbon atoms, halogen atom, formyl group, acetyl group or haloacetyl group, provided that in the group of the formula (XV) the nitrogen atom may form a salt of a strong inorganic acid or a strong organic acid; $R_{11}$ is hydrogen atom or fluorine atom; and $R_{12}$ is halogen atom, lower alkyl group, lower haloalkyl group or lower alkoxy group.

11. A composition according to claim 10, wherein A is the group of the formula (XV).

12. A composition according to claim 11, wherein R is the group of the formula (II), (III), (IV), (V), (VI), (XII) or (XIII).

13. A composition according to claim 11, wherein R is the group of the formula (VII), (X), or (XI).

14. A composition according to claim 11, wherein R is the group of the formula (VIII).

15. A composition according to claim 10, wherein A is the group of the formula (XVI).

16. A composition according to claim 15, wherein R is the group of the formula (II), (III), (IV), (V), (VI), (XII) or (XIII).

17. A composition according to claim 15, wherein R is the group of the formula (VII), (X) or (XI).

18. A composition according to claim 15, wherein R is the group of the formula (VIII).

19. An insecticidal or acaricidal composition according to claim 10, further comprising a synergist selected from the group consisting of N-octylbicycloheptenedicarboxyimide, N-octylbicycloheptenedicarboxyimide with arylsulfonate, N-octyl-1-isopropyl-4-methyl-bicyclo(2,2,2)octo-5-ene-2,3-dicarboxyimide, octachlorodipropylether, and piperonylbutoxide for enhancing the insecticidal effect or acaricidal effect of the insecticidal or acaricidal composition.

20. A method for killing insects or acarina by treating with insecticides or acaricides comprising as an essential ingredient an insecticidally or acaricidally effective amount of a compound of the formula (I):

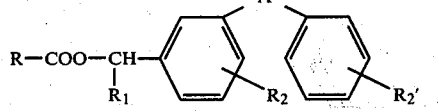

(I)

wherein R is the group (II), (III), (IV), (V), (VI), (VII), (VIII), (IX), (X), (XI), (XII) or (XIII):

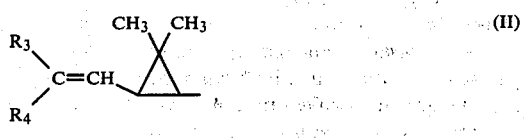

(II)

-continued (III)

(IV)

(V)

(VI)

(VII)

(VIII)

(IX)

(X)

(XI)

(XII)

(XIII)

wherein $R_3$ and $R_4$, which are the same as or different from each other, are methyl group, halogen atom or halomethyl group, or $R_3$ and $R_4$ together may form the ring:

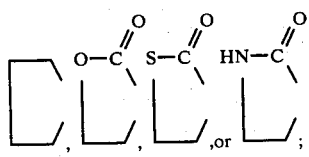

X is halogen atom; $R_5$ is $C_1$-$C_3$ alkyl group; n is an integer of 1-3; $R_6$ is hydrogen atom, methyl group, halogen atom or cyano group; Y is hydrogen atom, halogen atom, lower alkyl group, lower alkoxy group, lower alkylthio group, lower haloalkyl group, lower haloalkoxy group, lower haloalkylthio group or methylenedioxy group; z is methyl group, fluorine atom or chlorine atom; $R_7$ is methyl group or chlorine atom; $R_8$ is methyl group, chlorine atom, halomethyl group, methoxy group or methoxymethyl group, or $R_7$ and $R_8$ together may form ethylene-, trimethylene-, or tetramethylene-chain; $R_9$ is $C_1$-$C_6$ alkyl group or cycloalkyl-, alkenyl-, haloalkyl-, haloalkenyl-, or alkynyl- group, or the group of the formula (XIV):

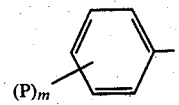

(XIV)

wherein m is an integer of 1-2; P is hydrogen atom, halogen atom, lower alkyl group, lower alkoxy group, lower alkylthio group, lower haloalkyl group, lower haloalkoxy group or methylenedioxy group; $R_1$ is hydrogen atom, cyano group, methyl group or ethynyl group; $R_2$, $R_2'$ are hydrogen atom, halogen atom, methyl group, trifluoromethyl group or lower alkoxy group; A is the group of the formula (XV) or (XVI):

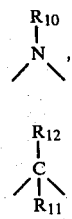

(XV)

(XVI)

wherein $R_{10}$ is hydrogen atom, alkyl- or haloalkyl- group having 1-2 carbon atoms, halogen atom, formyl group, acetyl group or haloacetyl group, provided that in the group of the formula (XV) the nitrogen atom may form a salt of a strong inorganic acid or a strong organic acid; $R_{11}$ is hydrogen atom or fluorine atom; and $R_{12}$ is halogen atom, lower alkyl group, lower haloalkyl group or lower alkoxy group.

* * * * *